US012201981B2

(12) United States Patent
Pizzi et al.

(10) Patent No.: US 12,201,981 B2
(45) Date of Patent: Jan. 21, 2025

(54) MICRO-FLUIDIC DEVICE FOR CONCENTRATION OF PARTICLES

(71) Applicant: ELTEK S.P.A., Casale Monferrato (IT)

(72) Inventors: Marco Pizzi, Casale Monferrato (IT); Giovanni Melioli, Casale Monferrato (IT); Valentina Gallo, Casale Monferrato (IT); Massimo Zanin, Casale Monferrato (IT)

(73) Assignee: ELTEK S.p.A., Casale Monferrato (IT)

( * ) Notice: Subject to any disclaimer, the term of this patent is extended or adjusted under 35 U.S.C. 154(b) by 854 days.

(21) Appl. No.: 16/972,255

(22) PCT Filed: Jun. 5, 2019

(86) PCT No.: PCT/IB2019/054683
§ 371 (c)(1),
(2) Date: Dec. 4, 2020

(87) PCT Pub. No.: WO2019/234657
PCT Pub. Date: Dec. 12, 2019

(65) Prior Publication Data
US 2021/0154671 A1 May 27, 2021

(30) Foreign Application Priority Data
Jun. 6, 2018 (IT) .................. 102018000006089

(51) Int. Cl.
*B01L 3/00* (2006.01)
*C12Q 1/18* (2006.01)
(Continued)

(52) U.S. Cl.
CPC ..... *B01L 3/502761* (2013.01); *B01L 3/50273* (2013.01); *B01L 3/502753* (2013.01);
(Continued)

(58) Field of Classification Search
None
See application file for complete search history.

(56) References Cited

U.S. PATENT DOCUMENTS 6,030,581 A * 2/2000 Virtanen .............. C12Q 1/6834
422/50
7,935,318 B2 * 5/2011 Harding ............... G01N 35/025
422/507

(Continued)

FOREIGN PATENT DOCUMENTS

JP    2003-533681 A    11/2003
JP    2006-055809 A    3/2006
(Continued)

OTHER PUBLICATIONS

International Search Report and Written Opinion of the ISA for PCT/IB2019/054683, mailed Sep. 26, 2019, 12 pages.

*Primary Examiner* — Samuel P Siefke
*Assistant Examiner* — Henry H Nguyen
(74) *Attorney, Agent, or Firm* — Nixon & Vanderhye P.C.

(57) ABSTRACT

A microfluidic device for concentrating particles contained in a fluid sample comprises a substrate (11) having a surface where at least one microfluidic arrangement (M) is defined, which comprises: —a loading chamber (14), for loading the fluid sample into the at least one microfluidic arrangement (M); —a plurality of microchannels (13), which have respective inlet ends connected to the loading chamber (14); and —a covering element (12), which is substantially impermeable to the fluid sample and extends at least partially over the plurality of microchannels (13). The loading chamber (14) and the microchannels (13) extend substantially according to a plane identified by the substrate (11), and the microchannels (13) are partially delimited, in particular at an accumulation region thereof (CA) generally opposite to the respective inlet ends, by filtering means (17) permeable at
(Continued)

least to air, the filtering means (17) being configured for withholding within each microchannel (13) any possible particles that may be present in the fluid sample.

19 Claims, 18 Drawing Sheets

(51) Int. Cl.
  *G01N 1/40* (2006.01)
  *G01N 21/64* (2006.01)
(52) U.S. Cl.
  CPC ............ *C12Q 1/18* (2013.01); *G01N 1/4077* (2013.01); *G01N 21/6428* (2013.01); *B01L 2200/0652* (2013.01); *B01L 2200/0668* (2013.01); *B01L 2200/0684* (2013.01); *B01L 2300/048* (2013.01); *B01L 2300/0663* (2013.01); *B01L 2300/0681* (2013.01); *B01L 2300/0803* (2013.01); *B01L 2300/0864* (2013.01); *B01L 2300/12* (2013.01); *B01L 2300/161* (2013.01); *B01L 2400/0409* (2013.01); *G01N 2001/4088* (2013.01); *G01N 2021/6439* (2013.01)

(56) References Cited

U.S. PATENT DOCUMENTS

| | | | | |
|---|---|---|---|---|
| 2002/0117517 A1* | 8/2002 | Unger | .................. | B01L 3/02 222/214 |
| 2002/0192701 A1* | 12/2002 | Adey | ................. | B01L 3/50273 435/293.1 |
| 2004/0253143 A1* | 12/2004 | Fukushima | ........... | B01L 3/5027 422/400 |
| 2010/0112723 A1* | 5/2010 | Battrell | .................. | G01N 33/53 422/68.1 |
| 2010/0129852 A1* | 5/2010 | Putnam | ................... | G01N 33/52 435/29 |
| 2011/0084708 A1* | 4/2011 | Yu | .......................... | G01N 33/03 73/864.72 |
| 2012/0156765 A1* | 6/2012 | Wimberger-Friedl | ...................... | B01L 3/502753 422/69 |
| 2014/0154687 A1 | 6/2014 | Talebpour et al. | | |
| 2014/0273070 A1* | 9/2014 | Hale | ....................... | G01N 1/40 435/283.1 |
| 2015/0273470 A1 | 10/2015 | Hoffmann | | |
| 2016/0041163 A1 | 2/2016 | Ding et al. | | |
| 2017/0080422 A1* | 3/2017 | Maaskant | .......... | B01D 19/0052 |
| 2017/0241878 A1 | 8/2017 | Broyer et al. | | |
| 2017/0298456 A1 | 10/2017 | Holder et al. | | |
| 2019/0388887 A1* | 12/2019 | Le Berre | ............ | B01L 3/502715 |
| 2020/0030797 A1* | 1/2020 | Shartle | ............. | B01L 3/502715 |

FOREIGN PATENT DOCUMENTS

| | | |
|---|---|---|
| JP | 2016-500008 A | 1/2016 |
| JP | 2016-070827 A | 5/2016 |
| JP | 2017-522573 A | 8/2017 |
| WO | 01/87486 | 11/2001 |

\* cited by examiner

MICRO-FLUIDIC DEVICE FOR CONCENTRATION OF PARTICLES

This application is the U.S. national phase of International Application No. PCT/IB2019/054683 filed 5 Jun. 2019, which designated the U.S. and claims priority to IT Patent Application No. 102018000006089 filed 6 Jun. 2018, the entire contents of each of which are hereby incorporated by reference.

FIELD OF THE INVENTION

The present invention relates in general to techniques for detecting or estimating the amount of particles present in a fluid sample, in particular particles at low concentrations and in small volumes.

The invention has been developed with particular reference to microfluidic devices designed to be subjected to centrifugation, as well as to devices and methods for conducting examinations or analyses on fluid samples, preferably containing organic or biological particles or bacteria or micro-organisms, for example for rapid execution of antibiograms.

The invention may in any case also be applied to the detection of other types of particles that may be present in a fluid sample, not necessarily organic or biological fluids or particles, and not necessarily via centrifugation.

PRIOR ART

Various techniques are known for counting particles, for example cells, present in a sample of a fluid, for example a biological fluid. The systems most commonly used are of an optical type (with or without fluorescence), of an impedancemetry type, or of a static type by means of image recognition. These known systems in general require relatively large sample amounts and do not enable an efficient parallelisation of the measurement, such as a number of measurements carried out at the same time, i.e., they presuppose a considerable amount of the starting sample to be able to carry out many measurements in parallel and/or simultaneously.

Known systems based upon image-recognition techniques may be used for the analysis of small fluid samples, but do not enable parallelisation of a number of samples, with consequent lengthening of the measurement times unless investments are made, which, however, frequently prove anti-economic.

AIM AND SUMMARY OF THE INVENTION

In its general terms, the present invention has the aim of indicating devices and methods that make it possible to carry out, in a simple, rapid, and inexpensive way, quantification and/or identification of particles present at low concentrations and/or in small volumes in fluid samples, enabling in an equally simple and inexpensive way parallelisation between a number of samples, with advantages in terms of time and costs, as well as in terms of efficiency as regards sensitivity and reproducibility.

A further aim of the invention is to indicate methodologies that make it possible to carry out antibiograms (when micro-organisms are being measured), i.e., to obtain susceptibility profiles of at least one micro-organism, or microbe, or bacterium to antibiotics, in relatively short times, indicatively of some hours; an auxiliary aim of the invention is to indicate methodologies that enable simultaneous execution of a plurality of antibiograms.

The above aims are achieved, according to the present invention, by a microfluidic device for the concentration of particles, and by corresponding supports and methods, which present the characteristics specified in the annexed claims. The invention likewise regards centrifugation and/or detection devices, which can be used in combination with the aforesaid microfluidic device, as well as methodologies of analysis based upon the use of such a device.

As will emerge clearly hereinafter, the invention makes it possible to carry out in a simple and rapid way effective detections of amounts of particles in samples of relatively modest volume of the fluid of interest.

BRIEF DESCRIPTION OF THE DRAWINGS

Further aims, characteristics, and advantages of the invention will emerge clearly from the ensuing detailed description, with reference to the annexed drawings, which are provided purely by way of non-limiting example and in which.

DETAILED DESCRIPTION OF EMBODIMENTS

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment", "in one embodiment", "in various embodiments", and the like, that may be present in various points of this description do not necessarily refer to one and the same embodiment. Moreover, particular conformations, structures, or characteristics defined in the framework of the present description may be combined in any adequate way in one or more embodiments, even different from the ones represented. The reference numbers and spatial references (such as "top", "bottom", "upper", "lower", etc.) used herein are provided merely for convenience and hence do not define the sphere of protection or the scope of the embodiments. The same reference numbers are used in the figures to designate elements that are similar or technically equivalent to one another.

Figure 1:
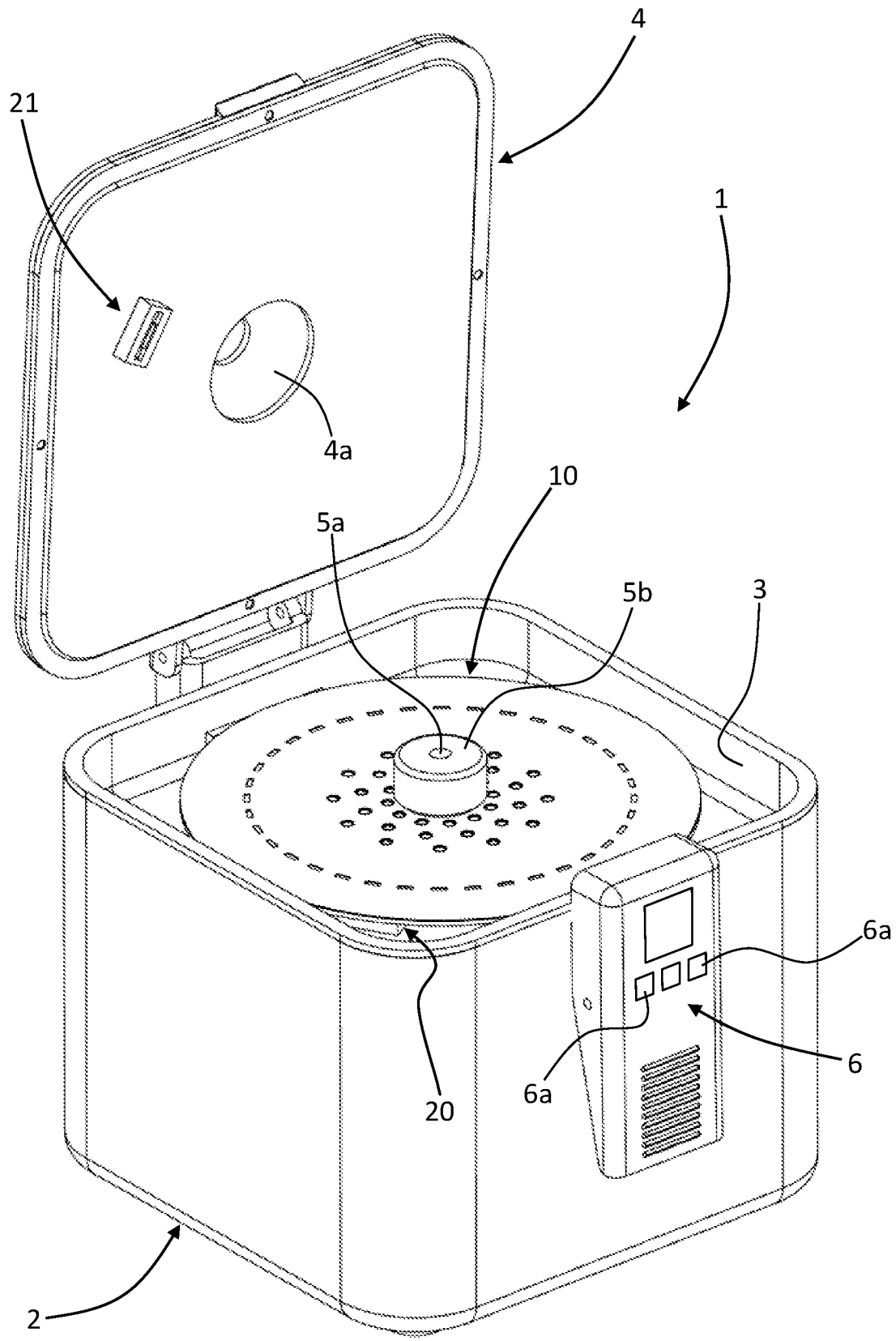
FIGS. 1 and 2 are schematic perspective views of a centrifugation and/or detection device and of a microfluidic device according to possible embodiments of the invention.
Figure 2:
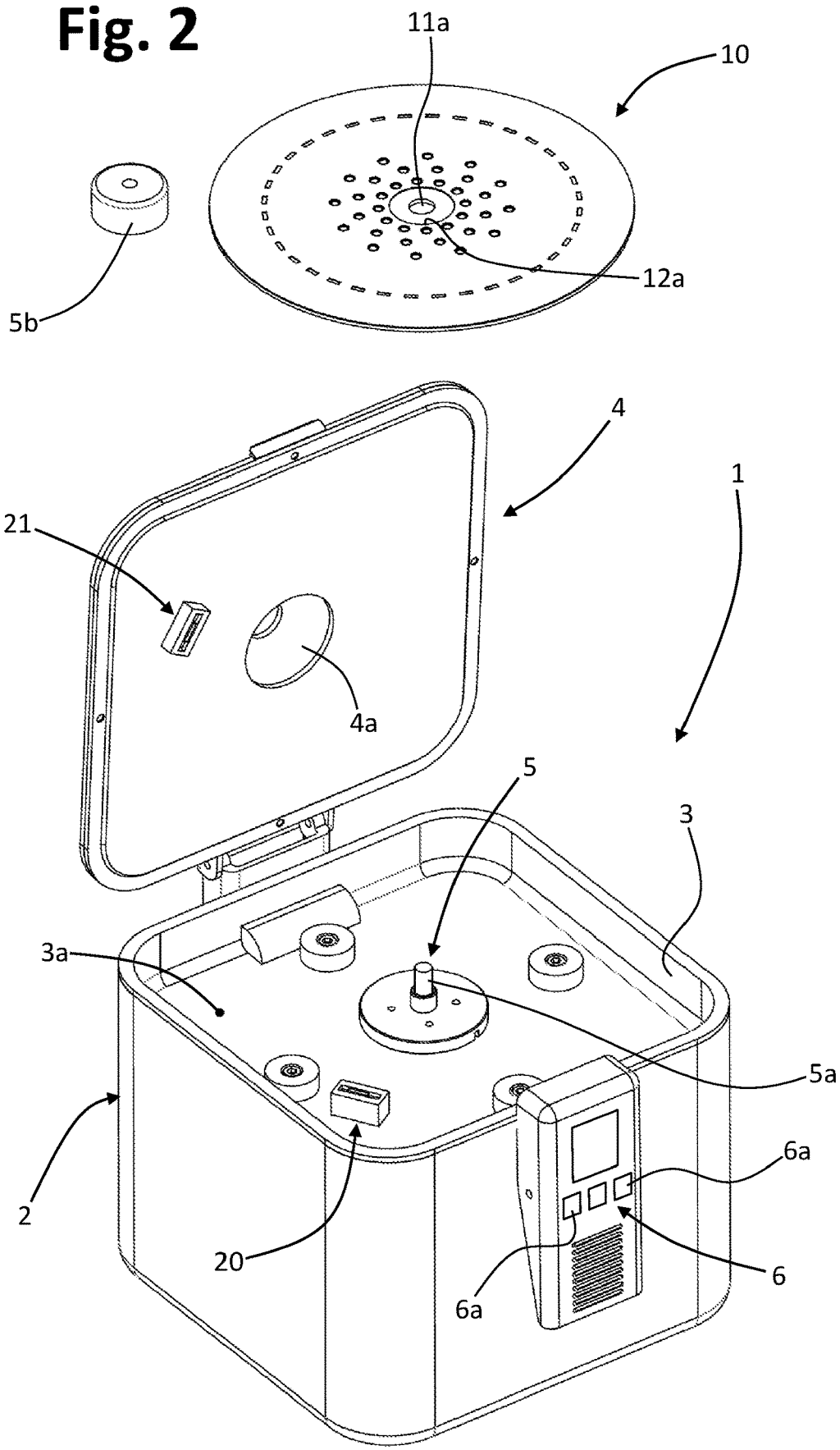

With initial reference to FIGS. 1 and 2, designated as a whole by 1 is a centrifugation and/or detection device, having a structure 2 that defines a treatment and/or detection chamber 3.

In various embodiments, the device 1 includes a lid or door 4, preferably hinged to the structure 2, for closing the chamber 3. The device 1 has a driving or movement system, designated as a whole by 5 in FIG. 2, which includes a rotating member 5a within the chamber 3, designed to set in rotation one or more microfluidic devices, preferably devices of a centrifugable type.

Possibly, the lid 4 may comprise a corresponding part 4a of a positioning and/or guide system of a centrifugable microfluidic device, or else of a support configured for supporting a plurality of centrifugable microfluidic devices. In the example, the part 4a includes a seat for a blocking and guiding element, designated by 5b, which can be coupled to the member 5a with the aforesaid centrifugable device or the aforesaid support set in between, in order to ensure mutual fixing in rotation between the parts referred to.

The actuation system 5 preferentially comprises an electric motor (partially visible in FIGS. 16-17, where it is designated by 5c), possibly provided with a motor reducer and/or an electronic control circuit. The centrifugation speed may indicatively be comprised between 200 and 1200 rpm, preferably between 400 and 1000 rpm, for times preferably comprised between 3 and 30 s, very preferably between 5 and 15 s.

In various embodiments, the device 1 comprises a system for control of the temperature and/or humidity within the treatment chamber 3. In various embodiments, this system is configured for maintaining a temperature higher than 25° C., preferably between 36° C. and 38° C., and/or a humidity that is preferably higher than 95%. In various preferred embodiments the device 1 comprises a suction system and/or a system for regulation of the pressure, pre-arranged for keeping the centrifugation area, or the chamber 3, at a pressure lower than ambient pressure and/or for forcing a flow of air at output from the aforesaid area or chamber into a filtering system configured for preventing diffusion of potentially contaminated aerosols into the environment.

In various embodiments, the device 1 includes a control panel, such as the one represented only in FIGS. 1 and 2, designated by 6, located on which are suitable control elements 6a for starting and/or stopping a process of centrifugation, and/or conditioning, and/or pressure regulation, and/or detection, and possibly for setting parameters of the aforesaid process (for example, centrifugation speed and/or time, and/or temperature, and/or humidity, and/or pressure in the chamber 3), as well as possible display and/or warning elements. The aforesaid control elements may be of any suitable type (pushbuttons, knobs, sliders, a touch display, etc.).

Figure 3:
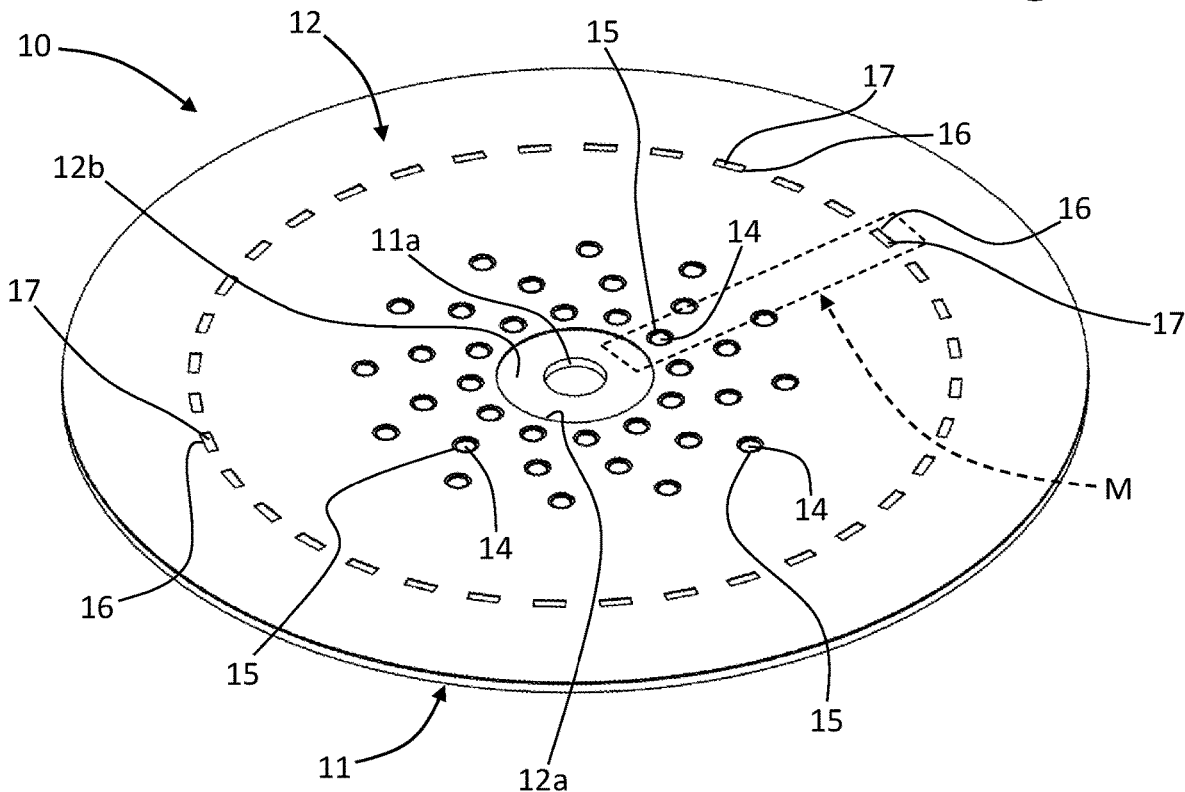
FIG. 3 is a schematic perspective view of a microfluidic device according to possible embodiments of the invention.

With reference also to FIG. 3, designated by 10 is a microfluidic device according to possible embodiments of the invention. In various embodiments, such as the one exemplified, the device 10 is configured for integrating or housing at least one arrangement designed to concentrate, via centrifugation, particles contained in a sample of a fluid substance. For this purpose, the device 10 includes or integrates at least one microfluidic arrangement, designated by M in FIG. 3, preferably a plurality of microfluidic arrangements. In what follows, for simplicity, initial reference will be made to the case of a device 10 provided with a plurality of microfluidic arrangements M, but in other embodiments described hereinafter the microfluidic device 10 according to the invention may include just one microfluidic arrangement.

Figure 4:
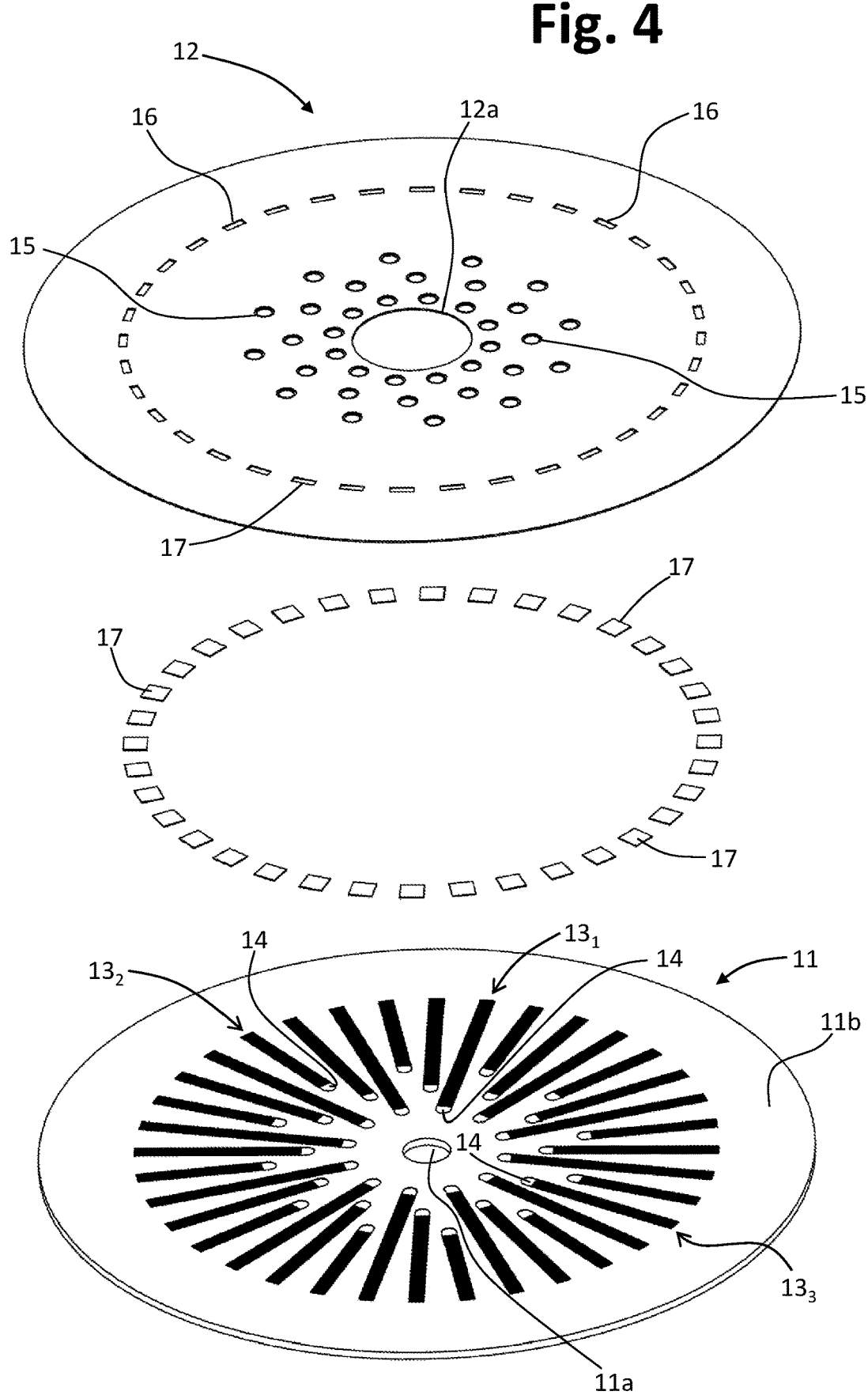
FIG. 4 is an exploded schematic view of a microfluidic device according to possible embodiments of the invention.

In various embodiments, and as exemplified in FIG. 4, the microfluidic device comprises a substrate 11 and a covering element 12, which define respective parts of a microfluidic arrangement M, or of each microfluidic arrangement M.

In various embodiments, the device 10 is configured for being set in rotation with respect to a centre of rotation, which is here assumed as being identified by the member 5a of the device 1 of FIGS. 1 and 2. For this purpose, in various preferential embodiments, the device 10 is disk-shaped and preferentially includes means 11a for coupling to the actuation system of a corresponding centrifugation device, for example, for coupling to the member 5a of the device 1 of FIGS. 1 and 2. In the case exemplified, the aforesaid coupling means 11a comprise a central passage or hole in the disk-shaped substrate 11. As will be seen, on the other hand, the disk shape of the substrate 11 does not constitute an essential characteristic, this not discounting the fact that the substrate, in various embodiments, is to be set in rotation with respect to a centre of rotation.

In various embodiments, the substrate 11 has a relatively small thickness, for example comprised between 0.5 and 4 mm. The substrate may, for example, be made of glass or plastic (for instance, polycarbonate, or polyethylene, or cycloolefin copolymers or COCs) and have a diameter indicatively comprised between 10 and 30 cm, hence possibly being similar to a classic compact disk. The materials used are preferentially electrically insulating materials, very preferably materials that are at least in part transparent.

In various embodiments, also the covering element 12 has a relatively small thickness, for example comprised between 0.1 and 0.5 mm. The covering element 12 may, for example, be made of polycarbonate or COC or polyethylene or glass, and have a diameter similar to that of the substrate 11, for example indicatively comprised between 10 and 30 cm.

The material or materials used for the covering element is/are preferentially substantially impermeable to air and to liquids. Also the covering element 12 may be disk-shaped, preferably provided with a central passage 12a that is to occupy a position concentric with respect to the passage 11a of the substrate 11 (see, for example, FIG. 3). The covering element 12 may, for example, be made of a flexible sheet material, which is glued or bonded on the substrate 11.

Figure 5:
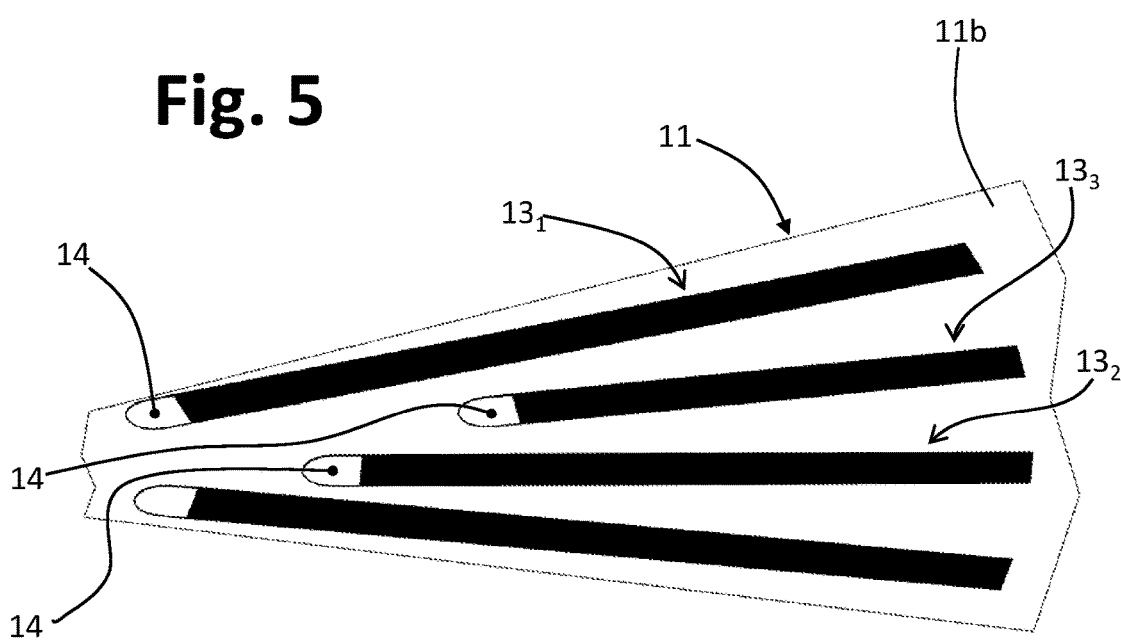
FIG. 5 is a detail at a larger scale of FIG. 4.

With reference to FIGS. 4 and 5, in various embodiments, the at least one microfluidic arrangement of a device according to the invention comprises a respective set of microchannels 13, defined in a surface 11b of the substrate 11 (which is here defined also conventionally as upper surface) on which the covering element 12 is applied.

In various preferential embodiments, the device 10 has a plurality of microfluidic arrangements, which are not necessarily the same as one another. For this purpose, on the substrate 11 a number of sets of microchannels 13 may be provided, each set belonging to a respective microfluidic arrangement. The microchannels 13 of different sets have preferably substantially the same length, even though this does not constitute an essential characteristic.

In various embodiments, a number of sets of microchannels 13 of various lengths are provided. For instance, in FIGS. 4 and 5, designated by $13_1$ is a set the microchannels of which have a maximum length, by $13_2$ is a set the microchannels of which have a minimum length, and by $13_3$ a set the microchannels of which have an intermediate length. Sets of microchannels having different lengths may, for example, be useful for optimising the occupation of the space available on the substrate 11, in particular with a substrate having the circular shape and/or with microfluidic arrangements or sets of channels 13 in substantially radial positions in order to have available on the substrate 11 a large number of microfluidic arrangements and hence be able to carry out in a convenient way parallelisation of a number of samples.

In various embodiments, such as the one exemplified, the microchannels 13 of each set extend in respective substantially radial directions with respect to the centre of rotation of the device 10, i.e., with respect to the central passage 11a of the substrate 11. The microchannels 13 of each set are preferably arranged side by side, preferably parallel to one another, and/or are preferentially substantially rectilinear. The microchannels 13 of each set extend preferentially according to a plane identified by the substrate 11, and for this purpose they can be defined on the surface 11b via a suitable technique, for example via micro-etching, or moulding, or polymerisation of resins by means of UV. In any case not excluded from the scope of the invention is formation of the microchannels via deposition of material on the substrate 11.

According to the preferential embodiment represented, the microchannels 13 of each set comprise at least one intermediate microchannel set in a radial position with respect to the centre of the passage 11a of the substrate 11, whereas the other microchannels of the same set are parallel to said intermediate microchannel, in a configuration in any case close to a radial arrangement, preferably parallel along both sides of the radial microchannel.

According to a further embodiment not represented, the microchannels 13 of each set comprise all the microchannels set radially with respect to the centre of the central passage 11a of the substrate 11; i.e., the microchannels 13 of each set are slightly angled with respect to one another, preferably mutually divergent at the end further away from the central passage 11, i.e., convergent at the end closer to the central passage 11a.

Each microchannel 13 has an inlet end and is pre-arranged for receiving a fluid sample. For this purpose, preferentially but not necessarily, each microfluidic arrangement M also comprises at least one loading chamber (which may also be in the form of a duct or channel), connected in fluid communication to which is the inlet end of each microchannel of a corresponding set 13.

Figure 6:
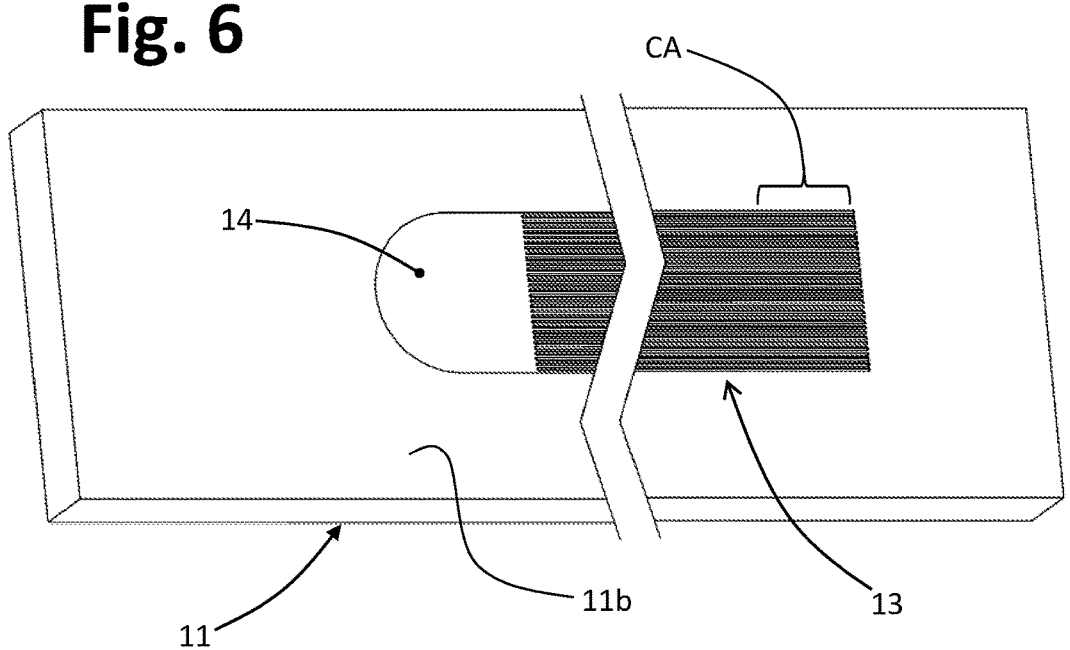
FIG. 6 is a partial and schematic perspective view of a part of microfluidic device according to possible embodiments of the invention.
Figure 7:
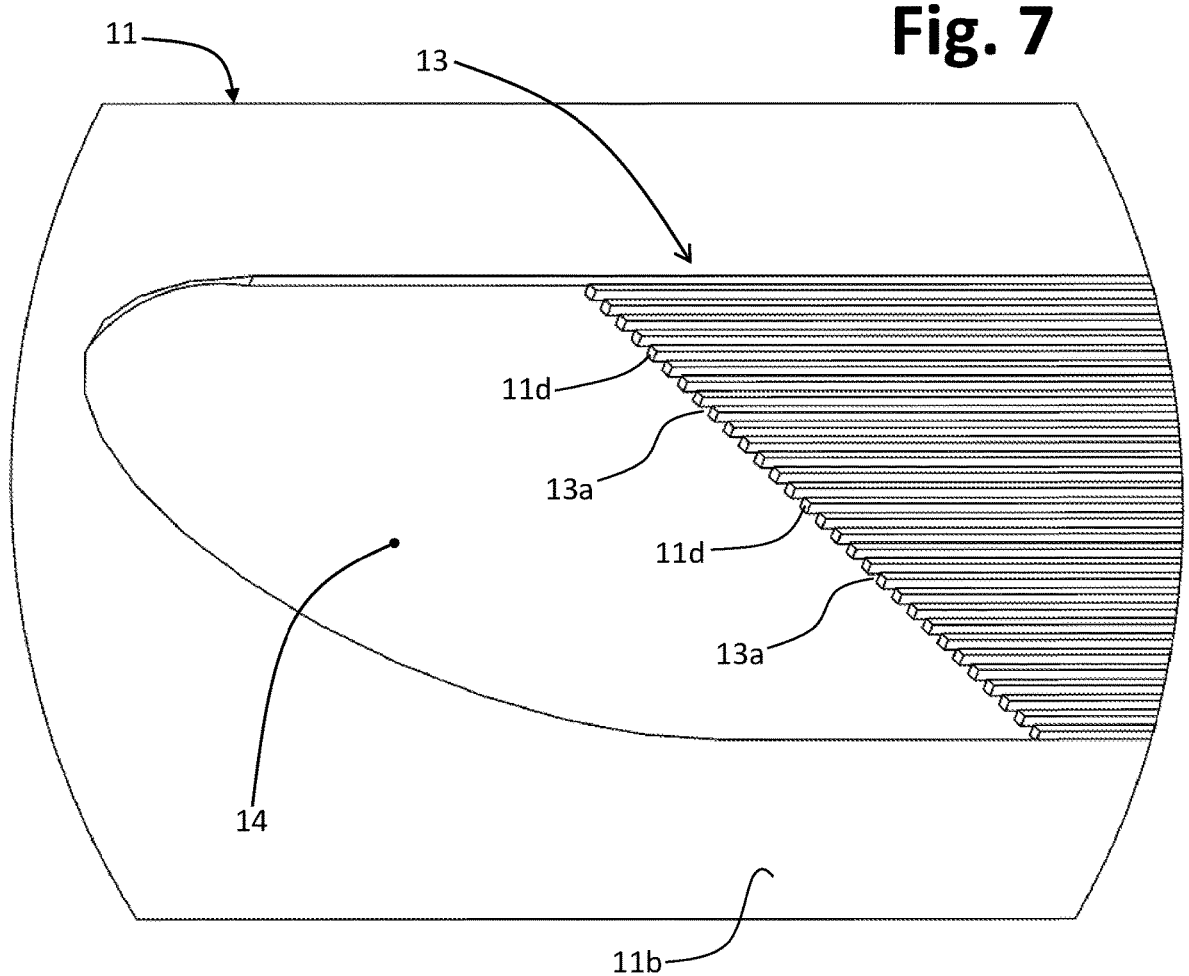
FIG. 7 is an enlarged detail of an end portion of a microfluidic arrangement according to possible embodiments of the invention.

Such a loading chamber is clearly visible, for example, in the details represented in FIGS. 6 and 7, where it is designated by 14. From FIG. 7 it may clearly be noted how the microchannels 13 have their inlet ends—some of which are designated by 13a—that are in fluid communication with the respective chamber 14, and how these inlet ends 13a are connected to the chamber 14 itself, preferably with a connection or an arrangement of the ends 13a in parallel or where they are set side by side. Hence, the microchannels 13 directly extend from the chamber 14.

In various embodiments, in particular those regarding microfluidic devices provided for centrifugation, the chamber 14 and the inlet ends 13a of the microchannels 13 of a given set are to be set in a position closer to the centre of rotation of the substrate 11, the opposite end of the microchannels being instead designed to occupy a position further away from the centre of rotation.

The microchannels 13 of each set are preferably at least in part the same as one another and/or extend at least in part substantially parallel to or equidistant from one another, for example parallel to or equidistant from one another in a substantially radial direction of the substrate 11. In various embodiments, the microchannels of one and the same set are substantially the same as one another in terms of shapes and size. According to other embodiments (not represented) sets may, instead, be provided the microchannels of which substantially have one and the same pattern, but have lengths different from one another.

From FIG. 7 it may be noted how, in various preferential embodiments, both the chamber 14 and the microchannels 13 are obtained from cavities or surface etchings made in the substrate 11, the microchannels 13 being in particular in the form of micro-grooves. In general terms, each microchannel 13 may have a width of between 5 and 200 μm, preferably between 15 and 50 μm, and/or a depth or height of between 2 and 100 μm, preferably between 5 and 40 μm. The length of each microchannel 13—understood as the distance between its two ends—may indicatively be between 5 and 50 mm. It is preferable for the microchannels 13 of one and the same set to have a constant section of passage, for homogeneity of analysis. Indicatively, the walls or portions in relief that separate the microchannels 13 from one another—some of these walls or portions being designated by 11d in FIG. 7—may have a width of between 5 and 200 μm, preferably between 15 and 100 μm.

In various preferential embodiments, the chamber 14 has a depth equal or close to that of the microchannels 13, for example a depth of between 2 and 100 μm, preferably between 5 and 40 μm.

As already mentioned, each microfluidic arrangement comprises a covering element 12, which at least partially covers the microchannels 13 of the corresponding set of microchannels. The covering element 12 may be made at least in part of a transparent material, for example glass or a plastic material, in order to enable viewing of the underlying microchannels 13, for example for the purposes of optical detection or of lighting. This does not constitute, however, an essential characteristic of the invention, for example when the substrate 11 is made of transparent material, at least in a part thereof defining a set of microchannels 13 or in a part thereof defining an end region of the microchannels 13 of a given set.

In various embodiments, such as the ones so far described, one and the same covering element is configured for covering at least partially a plurality of sets of microchannels 13. With reference, for example, to the case of FIGS. 3 and 4, provided on the substrate 11 are thirty-six sets of microchannels 13, each comprising a plurality of microchannels set side by side or parallel to one another, which have different lengths and are oriented in respective substantially radial directions, which are all at least partially covered by one and the same covering element 12.

According to other embodiments, each microfluidic arrangement may include one or more individual covering elements, with the element or each element that covers a single set of microchannels 13 at least partially.

Figure 9:
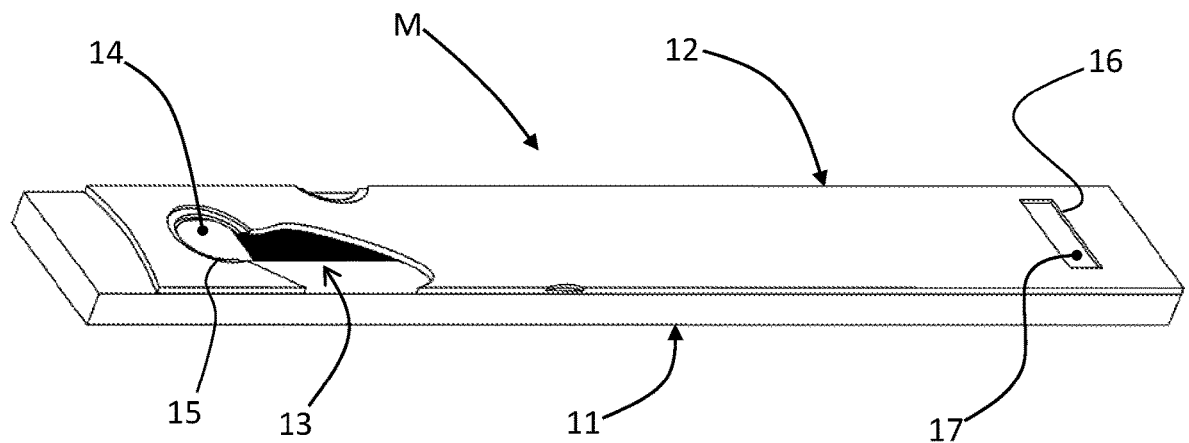
FIG. 9 is a schematic perspective view, partially sectioned, of a microfluidic arrangement according to possible embodiments of the invention.
Figure 10:
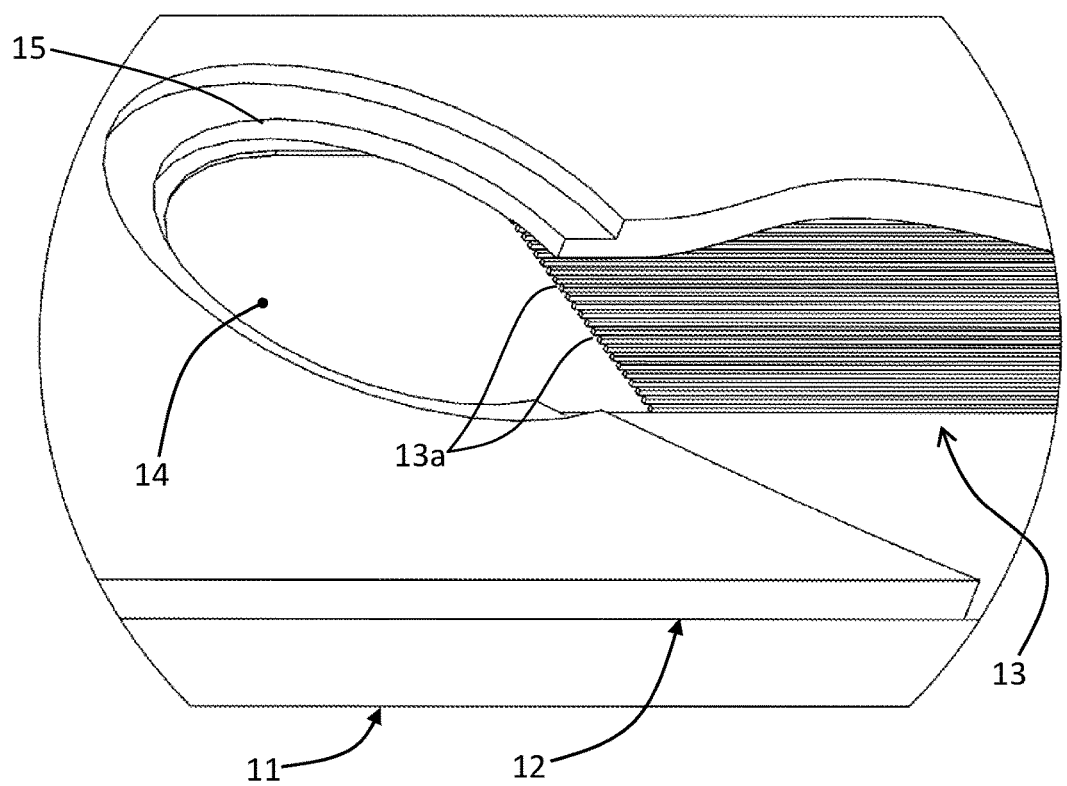
FIG. 10 is a detail at a larger scale of FIG. 9.

The covering element 12 (or each covering element) is configured or sized for leaving at least one portion of each microfluidic arrangement M, and in particular at least one part of the chamber 14, exposed. For this purpose, in various embodiments, the covering element 12 has at least one loading opening or passage that, in the assembled condition of the device 10, is substantially at a corresponding chamber 14. This characteristic may be fully appreciated, for example, in FIGS. 8-10, where some of the loading passages are designated by 15. In the example, each loading passage 15 has a circular profile, but this shape is evidently not imperative. Likewise, the generally curved profile of the chamber 14 does not constitute an essential characteristic.

In various embodiments, the material of which the covering element 12 is made is hydrophilic to facilitate entry of the fluid by capillary into each microchannel 13 of one set, from the chamber 14 to the inlet ends 13a of the microchannels themselves. The material of which the microchannels 13 are made, or the material of the substrate 11, may in this case also be hydrophobic.

It is also possible for at least one surface of the microchannel 13 that extends throughout the whole length thereof to be made of hydrophilic material: for example, in a microchannel 13 with rectangular or trapezial cross section, at least one of the four walls that define the cross section of the microchannel will preferably be made of hydrophilic material, for example the wall defined by the covering element 12.

As already mentioned, both the substrate 11 and the covering element 12 may be transparent. For instance, the substrate 11 may be made at least in part of a transparent material to enable viewing of the microchannels 13, and the covering element 12 may be transparent to enable backlighting of the microchannels themselves.

In various embodiments, each microchannel 13 has, throughout its whole extent, at least a continuous portion of inner surface having hydrophilic characteristics. The continuity of a hydrophilic portion along the inner wall of the microchannel 13 may be useful during filling, which envisages, for example, deposition of a drop of the sample liquid in the chamber 14 (as represented schematically in FIG. 8). Contact with the hydrophilic portion causes filling of the microchannels 13 by capillarity. For this purpose, in various embodiments, the bottom wall and the side walls of the microchannels 13, and the corresponding chamber 14, are made of a single hydrophobic material, whereas a prevalent part of the upper walls of the microchannels (for example, their part formed by the covering element 12) is made of hydrophilic material. On the other side, as will be seen, each microfluidic arrangement is preferentially configured, at its end region opposite to the inlet end 13a of the microchannels 13, for countering exit of the liquid in the absence of stresses. Consequently, once each microchannel 13 is entirely filled, it is no longer subject to the flow of liquid inside it unless it is subjected to external forces, as explained hereinafter.

As mentioned previously, the substrate 11 of a device 10 does not necessarily have to be disk-shaped. Such a case may be appreciated from FIG. 8, which shows a microfluidic arrangement M having a substrate 11 with a shape sectioned substantially in the form of a parallelepiped, preferably planar, and a covering element 12 in the form of a foil that is also parallelepipedal.

Figure 12:
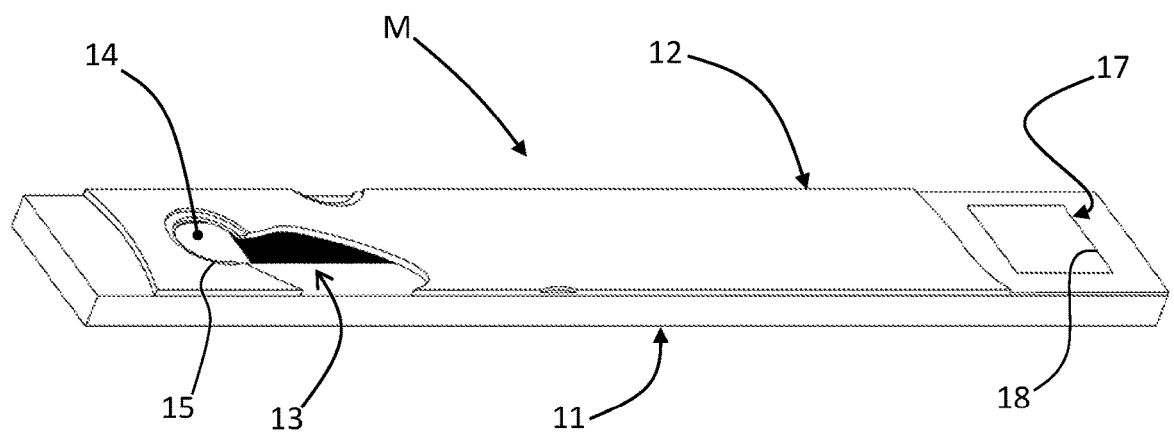
FIGS. 12 and 13 are partially sectioned schematic perspective views of a microfluidic arrangement according to possible embodiments of the invention.

As will be seen, substrates of this sort, i.e., not ones having a disk shape, may advantageously be pre-arranged for being treated—for example, via suitable supports or adapter elements—in a centrifugation device of a commercially available type, or else on a generic disk-shaped support that is to be coupled to the rotating member 5a of the device 1 of FIG. 1. It should in any case be noted that FIG. 8 (as likewise the subsequent FIGS. 9, 12, and 13) may in any case be also understood as representing the portion of a larger microfluidic device, for example the rectangular portion designated by M of the device 10 of FIG. 3.

The microfluidic arrangement of a device according to the invention comprises, in an end region thereof generally opposite to the inlet ends of the microchannels, a passageway for enabling at least outlet of air from the microchannels themselves. According to the invention, provided between this passageway and the microchannels is a filter element permeable at least to air, which is configured for withholding within the microchannels themselves the particles of interest present in the fluid sample.

The meshes or the porosity of the filter element may hence be chosen, during production of the microfluidic device, according to the size of the particles that are to be analysed. In various embodiments, the filter element is also permeable to the liquid part of the sample fluid, for example to enable exit of the liquid part from the microchannels during centrifugation.

In various embodiments the covering element may also be configured to define at least part of a housing seat for the filter element; alternatively, a housing seat for the filter element could be obtained in the substrate 11.

In various embodiments the position of the filter element is generally an apical one, in particular in a position which is substantially at the end opposite to the end through which the fluid enters the microchannels. The microchannels can end at a portion of the filter element, or else extend as far as a successive area, further closed by the covering element impermeable both to liquid and gases.

In the first case, each microchannel may be completely filled by capillarity, whereas in the second case the area of the channel which extend beyond the filter element will initially remain full of air (unless filling is performed under conditions of vacuum or negative pressure, or the microchannel contains initially at least in part a neutral fluid). During centrifugation, centrifugal force compresses the air (or other fluid), causing thereby partial or total outflow thereof through the filter element. At the end of the centrifugation the particles will be concentrated at the end of the channel, in an area not covered by the filter element. This configuration is advantageous when the filter element is not transparent or is subject to introduce optical distortions that may worsen displaying of the pellet, i.e., of the particle mass or concentrated. In this way, the displaying can occur through transparent and flat surfaces.

Figure 11:
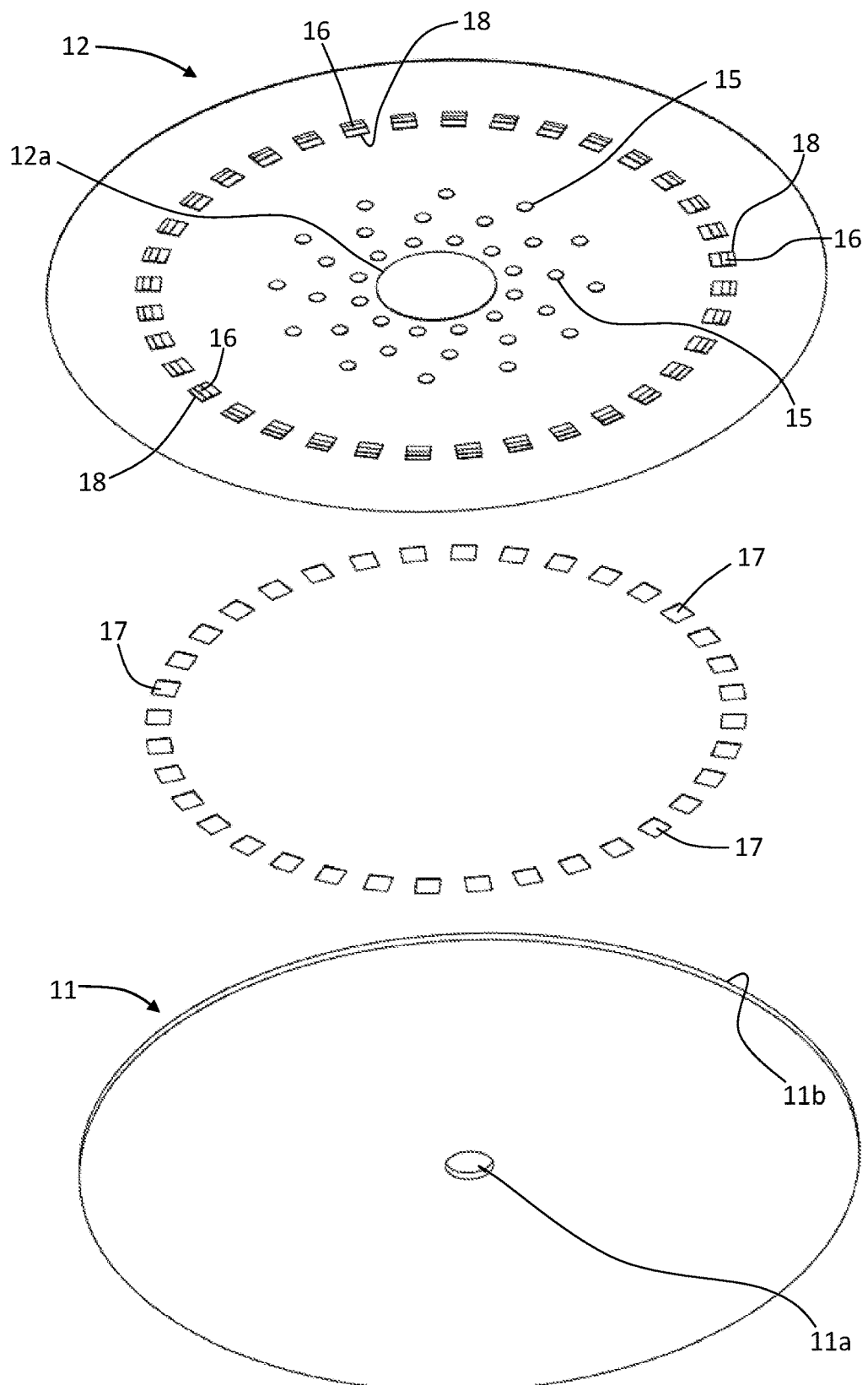
FIG. 11 is an exploded schematic view of a microfluidic device according to possible embodiments of the invention.

The covering element, which, as has been said, is configured for covering at least partially the microchannels of at least one microfluidic arrangement, may be sized or configured in order to define the aforesaid passageway. With reference, for example, to FIGS. 3, 4, 8, 9, and 11, in various embodiments, the covering element 12 defines a passageway 16 of a corresponding microfluidic arrangement M, where the passageway 16 is, for example, provided by a through opening of the element 12. In the case exemplified in FIGS. 3, 4, and 11, given that on the substrate 11 thirty-six sets of microchannels 13 are provided, the covering element 12 defines a corresponding number of passageways 16. In other embodiments, a single passageway 16 may be provided in a position corresponding to a plurality of sets of microchannels 13.

Once again with reference to the example of the above figures, given that the microchannels 13 of the various sets are substantially rectilinear, the passageway 16 and the loading passage 15 of one and the same microfluidic arrangement are substantially aligned with one another in the direction of extension of the corresponding microchannels 13.

In FIGS. 3, 4, 8, 9, and 11, designated 17 are some of the aforementioned filter elements permeable at least to air, which are to be positioned between the microchannels 13 of the various sets and the corresponding passageways 16. As may be seen in particular in FIGS. 11 and 12, in various embodiments, the covering element 12 may advantageously define a seat 18 configured for at least partial housing of a corresponding filter element 17. As exemplified (see, for instance, FIG. 11), such a seat 18 may be defined at a corresponding passageway 16, in particular in the side of the covering element 12 that is to face to the substrate 11.

Hence, in various embodiments, a microfluidic arrangement is configured in such a way that a corresponding filter element is kept in the operative position by the same covering element that covers at least partially the corresponding microchannels.

The filter element 17, or each filter element, is preferentially shaped like a membrane, with a porosity or mesh size of between 0.02 and 0.45 µm, preferably approximately 0.2 µm. A class of materials favoured in this sense are ceramic materials, for example alumina, which can be obtained with controlled porosity. In particular, alumina has an extremely low tendency to bind in a non-specific way with the dyes or fluorochromes typically used for marking cells. It is obviously possible to use other porous materials suitable for the purpose, such as plastic materials, which albeit generally presenting advantages in terms of costs, must be evaluated on a case-by-case basis in relation to the tendency to bind to the aforesaid marking dyes or fluorochromes and on the basis of the fluorescence itself of the polymeric material. In general, in the case where the micro-organisms or cells being analysed are previously marked with fluorochrome, the filter element 17 will be preferentially made of a material that does not bind in a non-specific way to the fluorochrome used and does not present autofluorescence that would cause a lowering of the signal-to-noise ratio.

In various embodiments, the thickness of the filter elements used is comprised between 20 and 1000 µm, preferably between 100 and 600 µm. The filter element is preferably optically transparent. Porous alumina tends to scatter the light and hence appears opaque and far from suitable as substrate of optical quality, but in the specific case, when its nanopores are full of water (refractive index of approximately 1.33) or other fluid with a refractive index more similar to that of alumina (refractive index of approximately 1.63 measured at 550 nm), the effect of scattering is considerably reduced, and the quality of the image that can be obtained through the wet alumina membrane is sufficient for detecting particles or cells in clear field or in fluorescence.

In the case exemplified, the elements 17 have a quadrangular shape, but this shape is not to be deemed essential: the shape of the filter element 17 may, in fact, be different according to the needs or of the type of the microfluidic device obtained.

Figure 8:
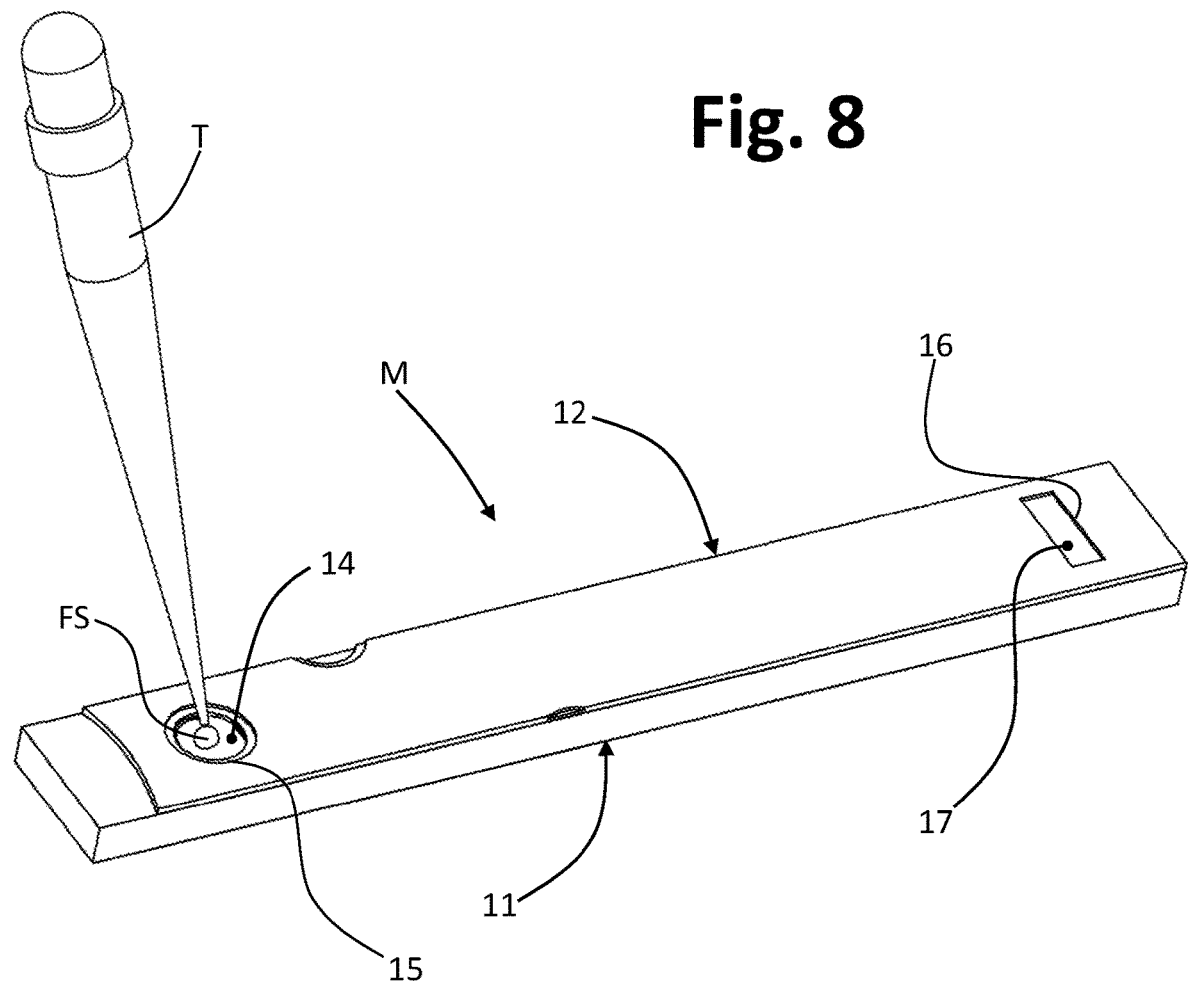
FIG. 8 is a schematic perspective view aimed at exemplifying a possible step of loading of a fluid sample into a microfluidic arrangement according to possible embodiments of the invention.

FIG. 8 shows schematically a possible mode of introduction of a fluid sample into the microfluidic arrangement M of a device according to possible embodiments of the invention. In the case exemplified, via a suitable tool T (such as a pipette designed to dispense a controlled amount of fluid, indicatively of the order of microlitres or tens of microlitres) a sample FS of the fluid that is to undergo examination is deposited in the chamber 14, through the corresponding loading passage 15, preferably defined at least in part in the covering element 12.

The sample FS may be a simple drop of the fluid, as in the case exemplified, or may even have a larger volume.

The chamber 14 and the passage 15 facilitate introduction of the fluid sample into the microfluidic arrangement M. Moreover, given that the arrangement M includes a plurality of microchannels 13, the chamber 14 basically functions as collector for introduction in parallel of the fluid into a number of microchannels. In other words, provision of a chamber 14, connected in parallel to which are the homologous ends 13a of a number of microchannels 13, presents the advantage of avoiding the need to introduce individually respective fractions of the sample into the single microchannels.

It should be noted that, as mentioned previously, the chamber 14 could be provided by a duct or a channel, via which the fluid sample is delivered to the inlet ends 13a of the microchannels.

The possibility of connecting a number of microchannels to one and the same inlet—whether it is a chamber, a passage, or a duct—makes it possible to increase the statistical basis of detection, i.e., to have available a number of repetitions of the same nominal conditions.

The number of microchannels to be used in the same nominal conditions will depend upon the type of use of the device and upon the volume of each microchannel: if, for example, a microchannel 13 were 2 cm long, with a width of 50 µm and a depth of 5 µm, the total volume would be $5 \cdot 10^6$ µm$^3$. With a concentration of $10^5$ bacteria/mL, there would be $10^{-7}$ bacteria per cubic micrometre. This means that in each microchannel there would be on average 0.5 bacteria. This also means that, in the microchannels that contain at least one bacterium, the signal could double after a very short time (approximately 20-40 min) in the cases of proliferation, and remain constant in those in which there is no proliferation.

This type of use may be referred to as "digital antibiogram". Since the microchannels are very small and may be defined in positions very close to each other, with a similar pattern, it is possible to have, on a very limited area (such as that of a single microscope slide), a multitude of channels, for example between 250 and 500 microchannels.

At concentrations like the ones just referred to, it would be expedient to dedicate to each n-tuplicate (i.e., set of n microchannels used in the same nominal conditions) at the same nominal concentration a number of microchannels comprised between 100 and 200 in order to have a sufficient statistical basis. On a single centrifugable device, for example a disk-shaped one, it would hence be possible to test a multitude (various tens) of different conditions, each of which is n-tuplicated, where n is comprised between 100 and 200. For higher concentrations, it will, instead, be possible to group in a smaller number of microchannels the conditions that are nominally the same. For instance, in the case of concentrations of the order of one million bacteria per millilitre it will be possible to use n-tuples of 10-20 microchannels for each nominally identical condition.

Figure 14:
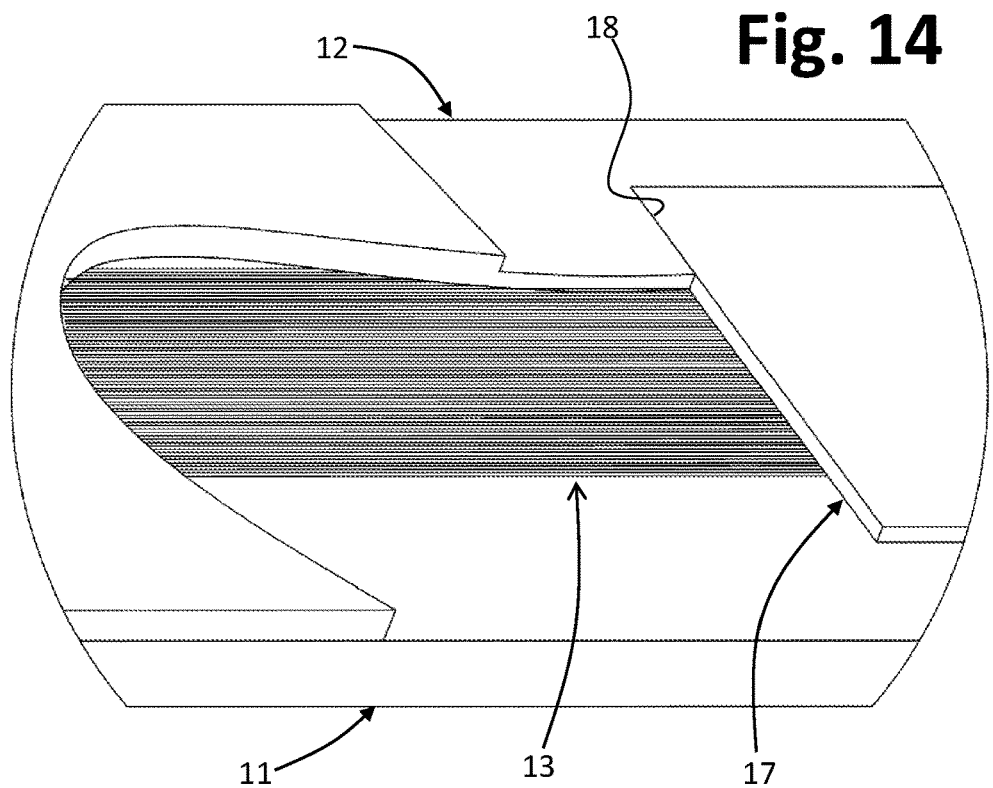
FIG. 14 is a detail at a larger scale of FIG. 13.
Figure 15:
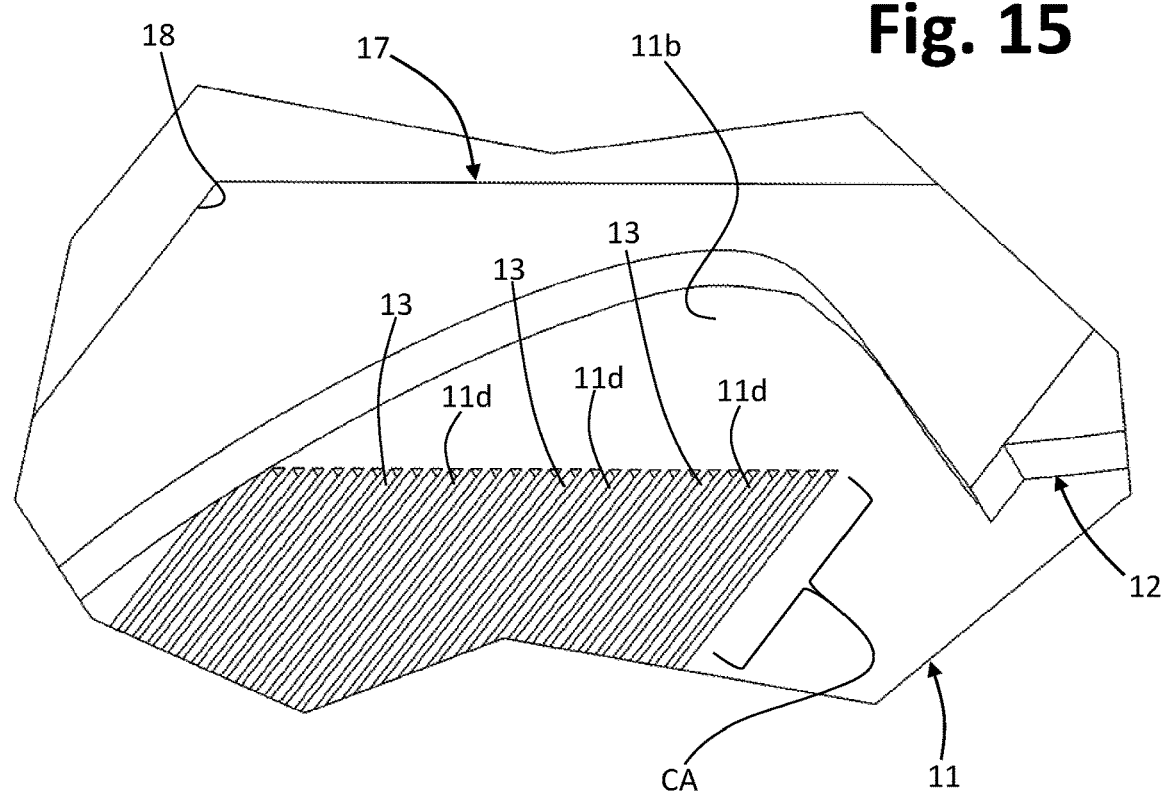
FIG. 15 is an enlarged detail of an end region of a microfluidic arrangement according to possible embodiments of the invention.

In various embodiments, each microchannel 13 is closed at its longitudinal end opposite to the inlet end 13a, for example as represented in FIG. 15, which illustrates an end region CA of a set of microchannels 13, with a corresponding filter element 17 sectioned. Embodiments of this sort may be used when set on top of at least the terminal stretch of the microchannels 13 is a filter element 17, as may be seen, for example, in FIGS. 13-15: the fluid can thus penetrate from the inlet end (13a, FIG. 10) of the microchannel 13, thanks to the fact that the air contained in the latter can progressively vent through the filter element 17. It should be noticed that the fluid which initially fills at least in part the microchannels 13 may be other than air (for instance a neutral liquid or gas, i.e., which does not alter the subsequent operations, this initial fluid being then replaced by the liquid containing the possible particles object of the analysis).

Figure 13:
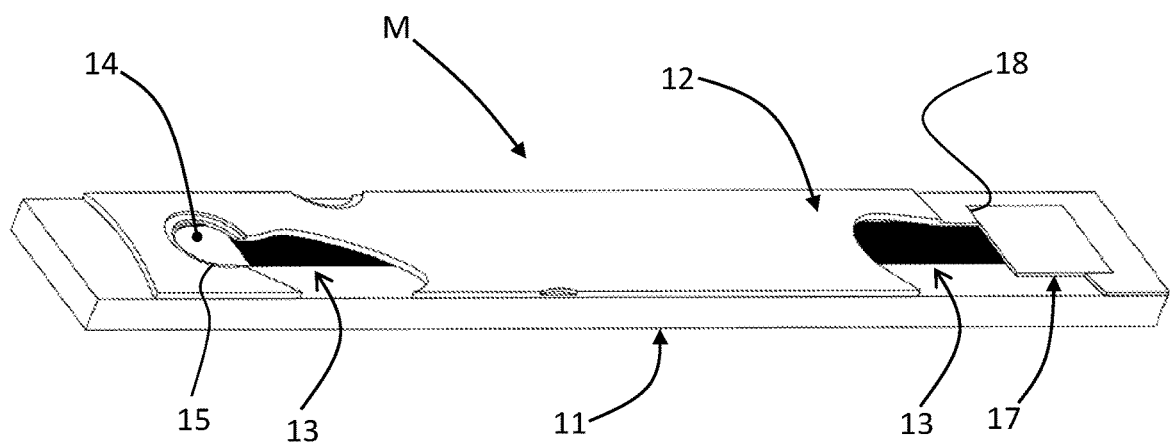

From FIGS. 13-15 it may be well noticed how one and the same filter element 17 may be superimposed to the plurality of microchannels 13, preferably but not necessarily in a position corresponding to the end regions CA thereof, which are parallel to one another and which are closed at their end opposite to the inlet ends 13a.

As has been said, in various embodiments, each microchannel 13 is preferably filled by capillarity or by exploiting the hydrophilicity of at least one of the walls or surfaces that delimit the microchannel itself. On the other hand, as will be seen, in other embodiments (not represented), the fluid sample could be forced under pressure into the microchannels, for example using a positive pressure or over-pressure at inlet or a negative pressure at outlet (always with respect to ambient pressure). As has been said, in the course of filling of a microchannel 13, the air originally contained therein can vent through the corresponding filter element 17 and the corresponding passageway 16, here defined in the covering element 12.

Figure 16:
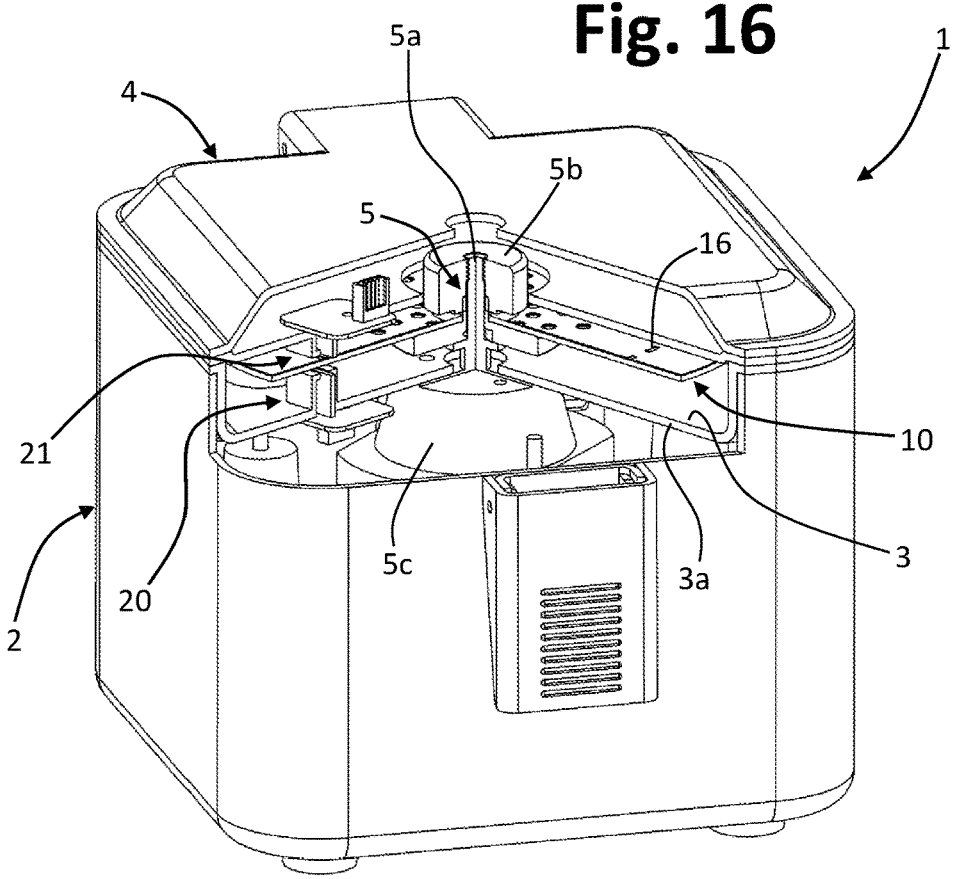
FIG. 16 is a partially sectioned perspective view of the device of FIGS. 1-2, with a corresponding microfluidic device in the operating condition.

With reference, for example, to the device 10 of FIG. 3, after introduction of the corresponding fluid sample into the chamber 14 of at least one arrangement M (as shown, for example, in FIG. 8), the microfluidic device is subjected to centrifugation, for example by means of a device 1 of the same type as the one represented in FIGS. 1 and 2. FIG. 16 illustrates the condition of installation of a device 10 of a disk-shaped type, such as the device of FIG. 3, in a centrifugation and/or detection device 1, with the door 4 of the latter in a closed condition.

Following upon rotation of the device 10, and as a result of the centrifugal force, the particles present in the volume of liquid that occupies a microchannel 13 will tend to accumulate at its end region CA, remaining prevalently within the channel itself; in particular, the particles will tend to accumulate at, or in the proximity of, the closed end of the corresponding microchannel and/or on its bottom wall and/or on its side walls in the end area CA, in the proximity of the filter element 17.

In the case where the filter element 17 is also permeable to liquid, the same liquid of the sample fluid will be able to exit from the microchannel 13, as a result of the centrifugal force, passing through the element 17 and the corresponding passageway 16, but in any case withholding the particles of interest in the end region CA of the microchannel.

According to various embodiments, in particular in the case of a filter element 17 permeable to liquid, at least part of the particles present in the volume of liquid contained in each microchannel 13 will tend to accumulate on at least part of the filter element 17 located in the end region CA of the respective microchannel 13, or on the portion of wall of the microchannel delimited by said portion of filter element 17.

Of course, the dimensions of the microchannels 13 must be sufficient to allow entry of the particles of interest therein. In general terms, relatively shallow microchannels are preferable, i.e., ones having a height or depth of the order of the size of the particles of interest or just slightly greater. The reason for this is that—given the same number and size of the particles—in the end region CA of a shallow microchannel 13 the amount of particles accumulated alongside one another will form an image in the plane having a larger area than a deeper microchannel, where the particles could lie on top of one another and thus falsify to a certain extent detection of the amount of particles and/or type thereof. The use of shallow microchannels, preferably with an approximately rectangular section, hence facilitates and improves the quality of reading of the amount and/or type using optical systems.

For instance, if a device 10 has to be used for separation of different types of whole blood cells, it is preferable for there to have a height (depth) of the microchannels 13 of between 10 and 40 µm, preferably between 10 and 20 µm. If the object of analysis are, instead, bacteria, the microchannels may have a height (depth) of between 3 and 10 µm, preferably between 4 and 8 µm. Again, in the case where yeasts are to be measured, the height (depth) of the microchannels will preferably be between 5 and 20 µm, most preferably between 8 and 12 µm.

In any case, thanks to the arrangement referred to, the particles possibly contained in a volume of the fluid that penetrates into a microchannel 13 tend to concentrate at the corresponding end region CA, both as a result of the centrifugal force undergone directly by the particles and caused by a rotation of the device 10 about the centre of rotation 5a and possibly as a result of the flow of the fluid and/or of emptying of the microchannel that entrains along with it the particles in suspension.

Detection or reading may be carried out by quantifying in an optical way the size of the mass of particles that, as a result of centrifugation, is formed in each end accumulation region CA. It is also possible to carry out such a detection of the amount and/or type by measuring the intensity of fluorescence, in the case where the particles have previously been marked with fluorochromes.

In various embodiments, the device 1 itself can integrate an optical detection arrangement. The optical arrangement may include a single sensor or else an array of sensors (for example, as in an optical scanner), or else a rectangular array of sensors, as for example a CCD or a CMOS sensor, with which it is possible to capture the image of the end area CA of the microchannel and analyse it in various ways, for example with automatic processing programs for counting particles. In general, then, one and the same device 1 can integrate functions of centrifugation and functions of detection or reading, in particular by exploiting rotation of the support 10 both for the aforesaid centrifugation that for the aforesaid reading using the optical detection arrangement.

Figure 17:
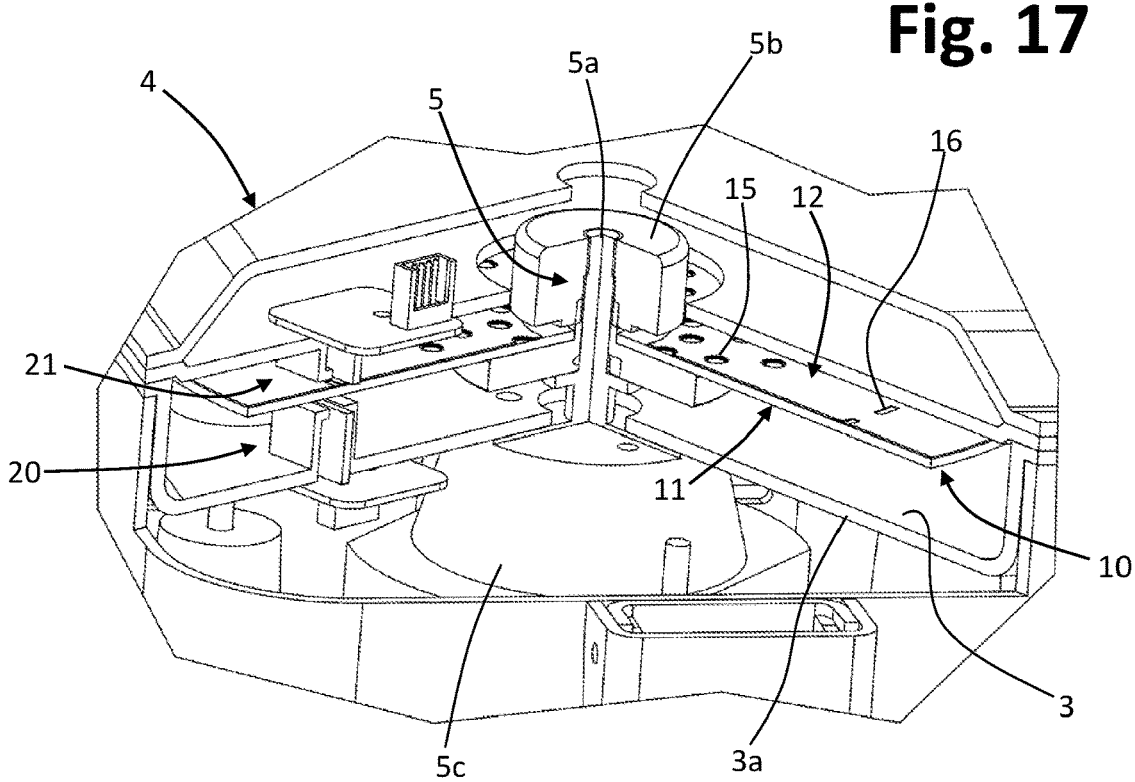
FIG. 17 is a detail at a larger scale of FIG. 16.

For instance, FIGS. 16 and 17 exemplify a centrifugation device 1 having a detection arrangement that includes at least one optical sensor 20, which preferably is itself constituted by an array of optical sensors. In the example, the sensor 20 is mounted stationary, in particular at a bottom wall 3a of the treatment chamber 3. The sensor 20 is at a distance from the centre of rotation 5a of the device 10 such that in front of the sensor itself there can pass the end regions CA (FIGS. 6 and 15) of all the microfluidic arrangements present on the disk-shaped device 10. In the case exemplified, the sensor 20 faces the side of the substrate 11 opposite to the covering element 12, and the substrate 11 is made of transparent material, at least at the aforesaid end regions CA of the various microfluidic arrangements M: in this way, the sensor 20 is in any case able to carry out the necessary optical detections. The optical sensor may be provided with the appropriate optics designed to focus and magnify the area of interest.

Possibly, at a part generally opposite to the optical sensor 20 a light source may be provided, in order to facilitate optical detection, or else another optical detection sensor. In the case exemplified, a light source 21 is associated to the inner side of the door 3 of the device 1, in a position such that—in the condition where the door is closed as represented in FIGS. 16-17—the source 21 illuminates at least the end region CA each time exposed to the sensor 20. Also for this purpose the filter element 17 may be made of a transparent material, or a material that it is transparent when it comes into contact with a liquid. A preferred material for providing the filter element 17 is, as has been said, porous alumina.

The control system of the device 1 may be pre-arranged for controlling the angular position of the microfluidic device 10 according to the optical detections to be carrying out each time. This control system may also be pre-arranged so as to carry out optical detections after the end of the centrifugation step, by driving and stopping each time the support 10 in the various angular reading positions, or else so that the optical detections are performed with the support 10 moving, preferably at low speed, such as a speed during detection or reading lower than the centrifugation speed, or by synchronising rotation with reading.

In other embodiments, for example with microfluidic devices provided with microfluidic arrangements oriented in a way different from the cases previously exemplified with reference to FIGS. 1-3, the optical sensor 20 can be mounted movable, for example via an actuator of its own, on a corresponding guide so that it can be displaced, for example in the radial direction relative to the device 10, for carrying out the necessary optical detections on a number of microfluidic arrangements. For such cases, the control system of the device 1 will be pre-arranged for controlling the position of the sensor 21 according to the optical detections to be carried out each time.

In various embodiments of the invention, the optical sensor means 20 of a centrifugation and/or detection device of the type referred to are configured for acquiring a cumulative optical signal or a cumulative image of a plurality of accumulation regions of the micro-fluidic device, i.e., a signal or image regarding all the accumulation regions CA of the microchannels 13 of a corresponding microfluidic arrangement M. The centrifugation and/or detection device is then pre-arranged, for example via suitable software, for processing, on the basis of the aforesaid optical signal or image, information representing an amount of particles that have accumulated in each of the individual accumulation regions CA of the various microchannels of one and the same microfluidic arrangement, in particular with a processing that enables estimation of the number of particles for each individual microchannel 13.

In other embodiments, for example when the optical sensor 20 includes an array of sensors, such as in an optical scanner, the sensor itself may be configured for acquiring an individual optical signal or an individual image of the accumulation region CA of each individual microchannel 13 of a corresponding microfluidic arrangement M. Also in this case, the centrifugation and/or detection device is pre-arranged for processing, on the basis of the aforesaid optical signal or image, information representing an amount of particles that have accumulated in each of the individual accumulation regions CA of the various microchannels of the microfluidic arrangement.

Of course, a device 1 may also be provided in order to be able to employ both of the techniques of optical detection (i.e., collective and individual) referred to.

Figure 18:
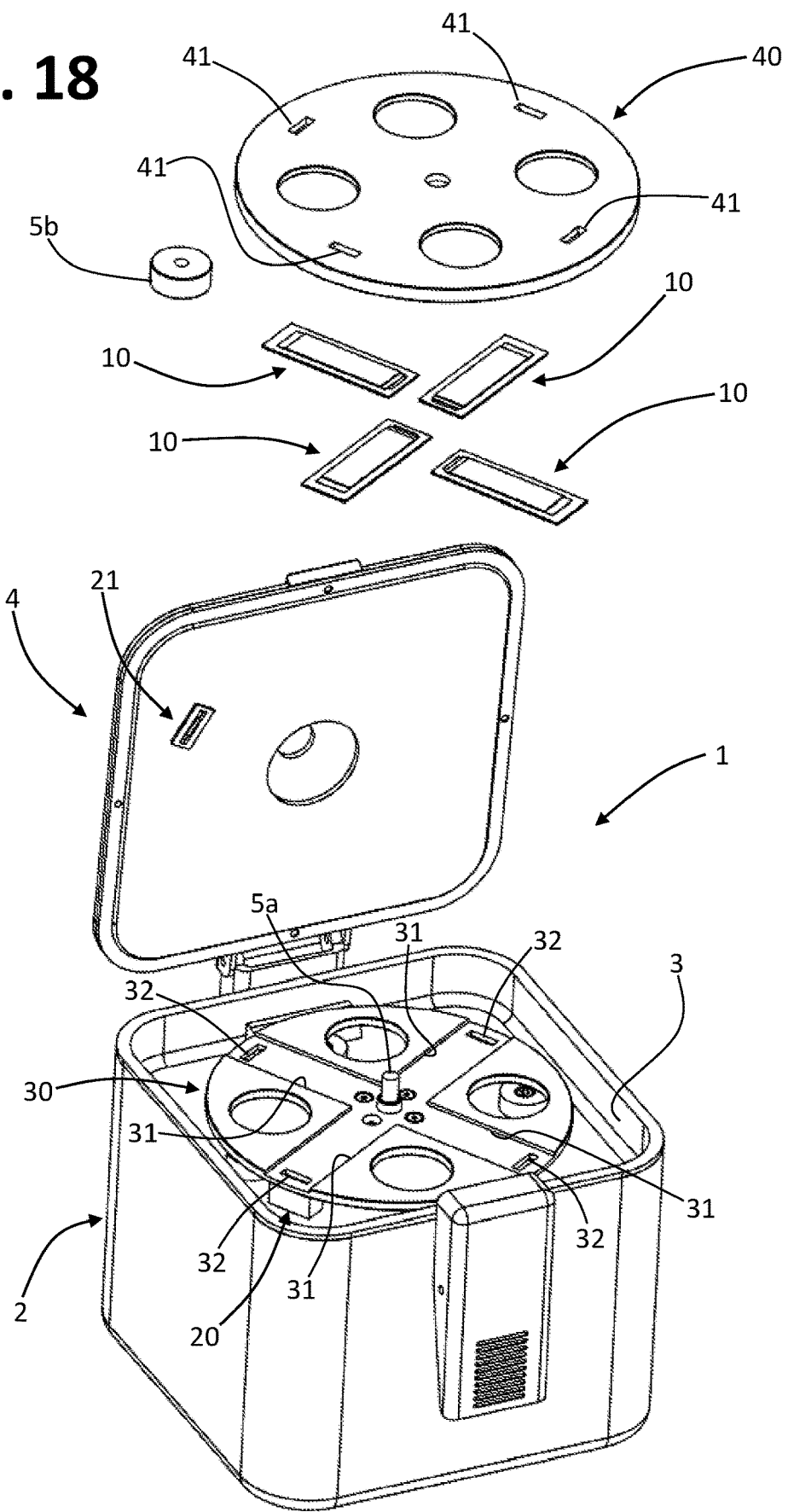
FIG. 18 is a schematic perspective view of a centrifugation and/or detection device and of some microfluidic devices according to possible embodiments of the invention.
Figure 19:
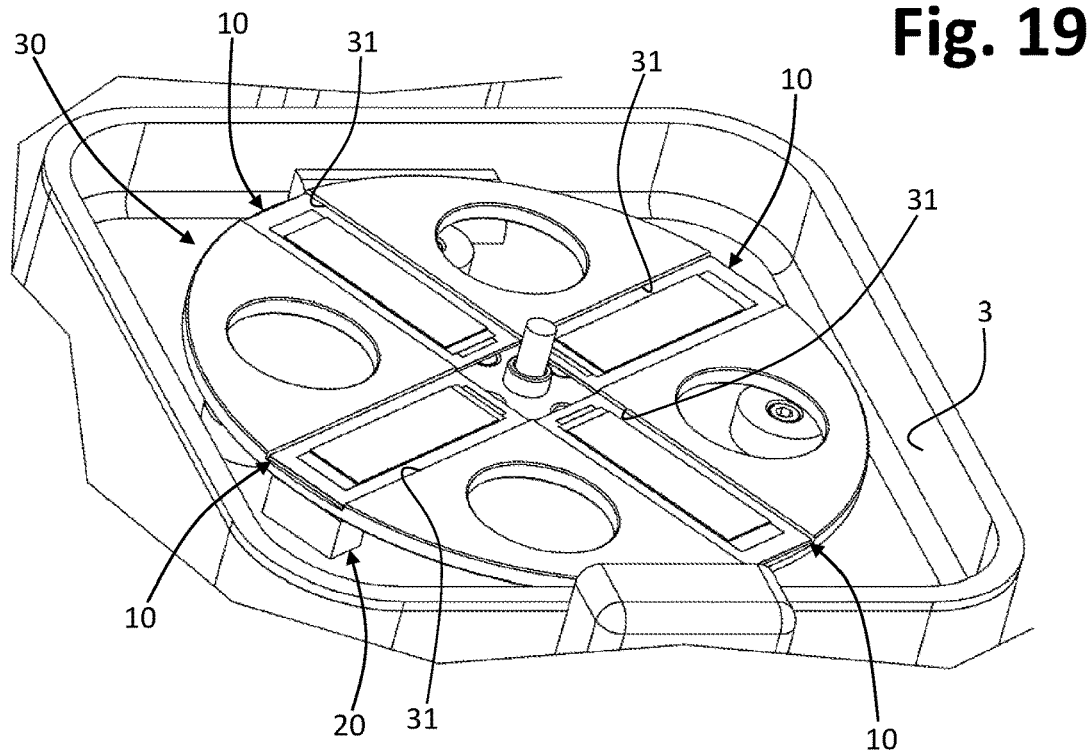
FIG. 19 is a detail at a larger scale of FIG. 18.
Figure 20:
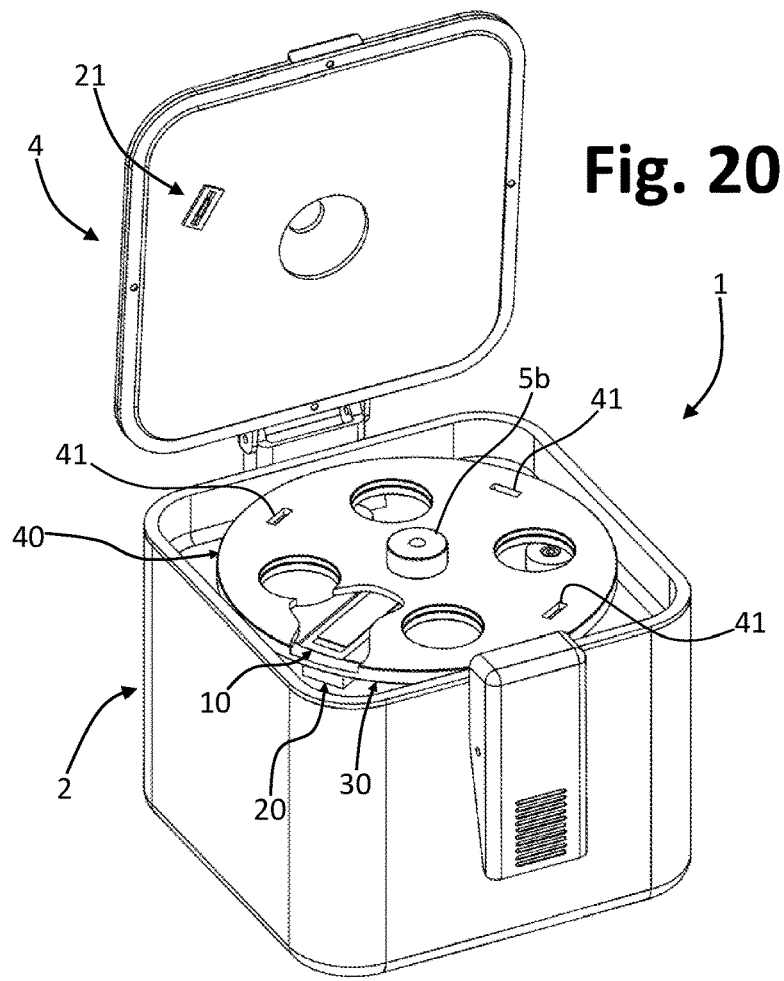
FIG. 20 is a partially sectioned schematic perspective view of the centrifugation device of FIG. 18, with corresponding microfluidic devices in the operating condition.

FIGS. 18-20 illustrate possible variant embodiments of a centrifugation and/or detection device 1 and of microfluidic devices 10.

In the case exemplified, the devices 10 have a generally quadrangular profile and preferentially each include a single microfluidic arrangement. Devices of this shape may, however, include also a number of microfluidic arrangements generally parallel to one another.

As may be seen in particular in FIG. 18, in various embodiments, the device 1 may be equipped with a centrifugation support 30, which defines one or more seats 31—preferably oriented in a substantially radial direction with respect to the centre of rotation 5a—that are each to receive at least one microfluidic device 10. In various embodiments, the support 30 has, at each seat 31, a passage 32 (such as an opening or a window or an optically transparent area) that is located in a position corresponding to the one assumed by the end detection region CA of the microchannels, when the corresponding device 10 is mounted on the support itself, as exemplified in FIG. 19. The aforesaid position of the passage 32 on the support likewise corresponds—in a radial direction—to the position of the sensor 20 of the device 1, so that the sensor is capable to carry out the necessary optical detections. The passages 32 make it possible to make the centrifugation support 30 of a non-transparent material, but there may possibly be present in a centrifugation support 30 made at least in part of transparent material.

In the non-limiting example represented, four seats 31 are provided, one for each device 10, each seat 31 being provided with a corresponding passage to enable detection by the optical sensor 20.

In various embodiments, in order to ensure positioning of the microfluidic devices 10 on the centrifugation support 30, the latter may be provided with an upper element, designated by 40 in FIG. 18, which closes the seats 31 from above ensuring maintenance of the position by the microfluidic devices 10. Also the upper element 40 may be provided with passages 41, such as openings or windows or optically transparent areas, in positions substantially corresponding to the end regions of the microfluidic arrangements of the devices 10, in order to enable lighting thereof by the light source 21.

FIG. 20 illustrates schematically the mounted condition of the support 30 with the corresponding upper element 40, and with the microfluidic devices 10 set in between, only one of which is visible at the sectioned part of the upper element 40. Operation of the device 1 of FIGS. 18-20 is similar, in relation to its functions of centrifugation and/or detection, to that of the devices 1 described with reference to FIGS. 1-2 and 16-17.

Figure 21:
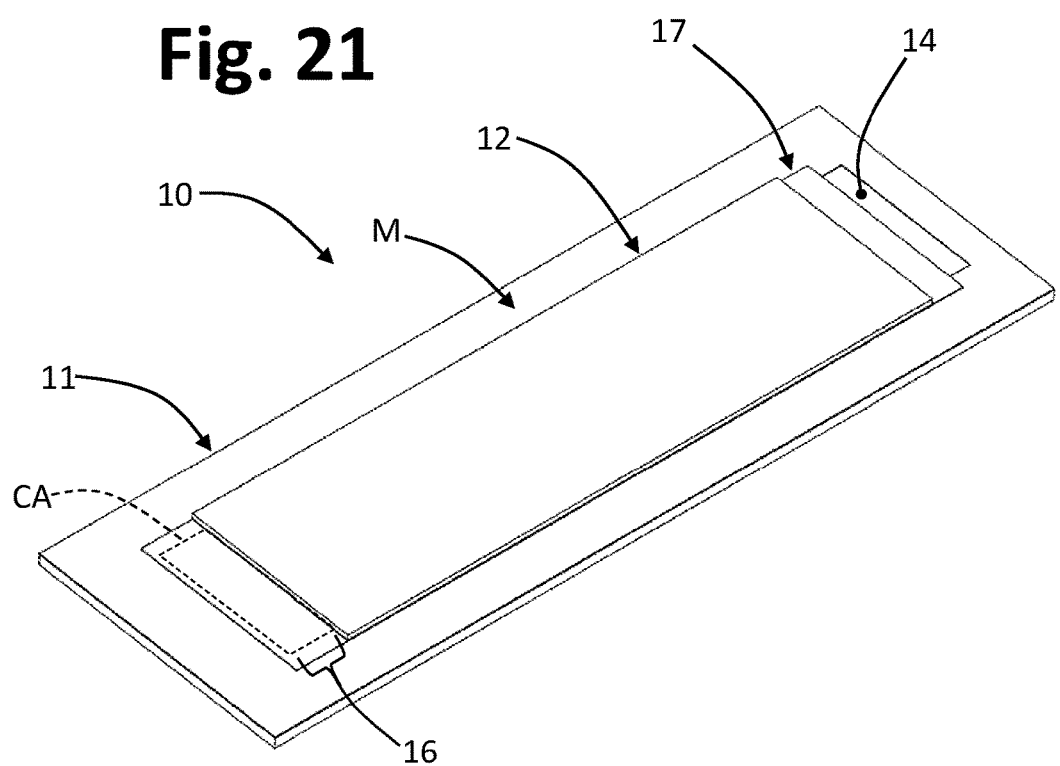
FIG. 21 is a schematic perspective view of a microfluidic device according to possible embodiments of the invention.

FIG. 21 illustrates a microfluidic device 10 with quadrangular profile, for example suitable for use on a centrifugation and/or detection device 1 of the type illustrated in FIGS. 18-20, i.e., designed for installation on the corresponding centrifugation support 30. In this case, the device includes a single microfluidic arrangement M which, as may be appreciated from FIG. 22 or from FIG. 23, in turn includes a set of microchannels 13 defined on a substrate 11, as well as a chamber 14, a covering element 12, and a filter element 17.

Figure 22:
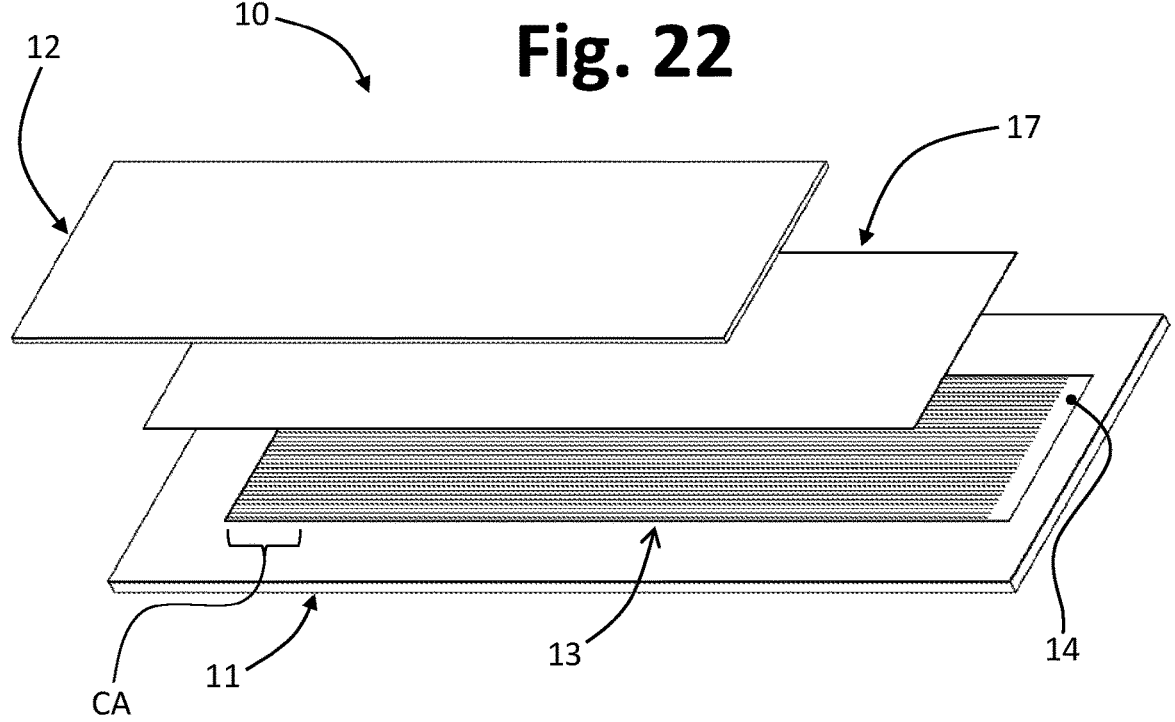
FIGS. 22 and 23 are exploded schematic views of microfluidic devices according to possible embodiments of the invention.

In the case exemplified in FIG. 22, the filter element 17, having a substantially rectangular profile, is sized so as to coat the microchannels 13 completely or practically completely, leaving at least part of the chamber 14 exposed. The material that constitutes the filter element 17 may advantageously be a hydrophilic material or a hydrophobic material, according to the needs, on the basis of what has been explained previously. The filter element 17 may be fixed in position on the substrate 11, for example, via gluing or bonding. On the filter element 17, and possibly in part on the substrate 11, the covering element 12, which here also has a substantially rectangular profile, is then fixed.

Figure 23:
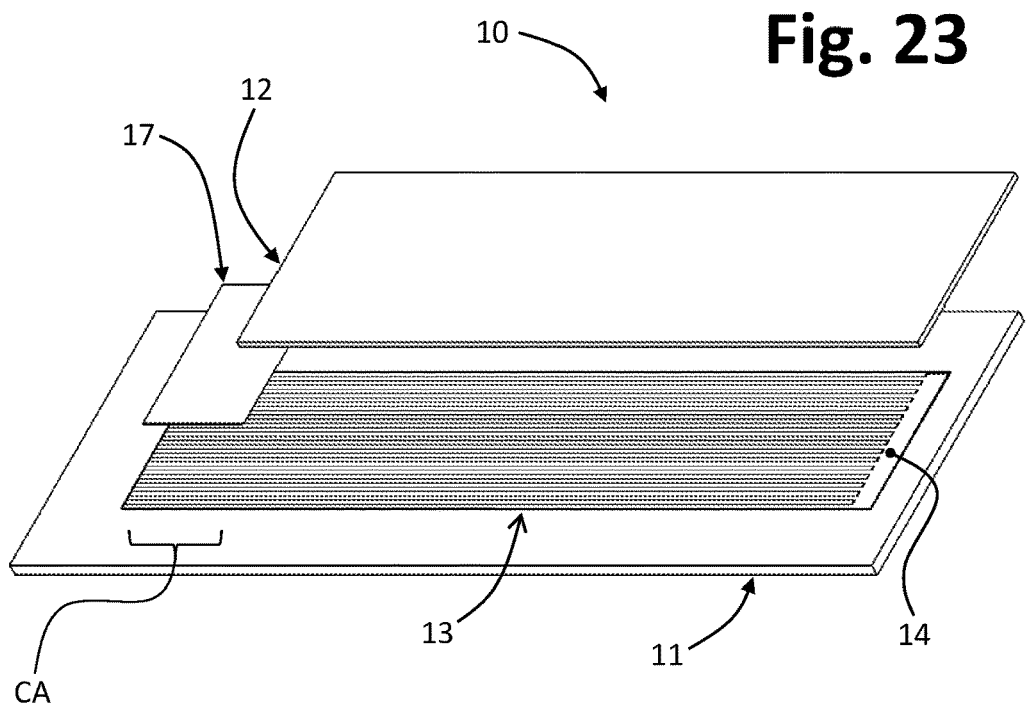

In the case exemplified in FIG. 23, the filter element 17, having a substantially rectangular profile, is sized so as to coat only an end area of the microchannels 13 that is opposite to the chamber 14. Also in this case, the filter element 17 can be fixed in position on the substrate 11, for example via gluing or bonding. On at least part of the filter element 17, and possibly in part on the substrate 11, there is then fixed the covering element 12, which here also has a substantially rectangular profile and in this case directly delimits the microchannels 13 in their upper part, at least for a substantial stretch thereof that extends between the filter element 17 and the chamber 14.

Both in the case of FIG. 22 and in the case of FIG. 23, the element 12 is sized so as to leave in any case exposed at least part of the chamber 14, as well as at least one end part of the filter element 17 in such a way that a passageway 16 will in any case be defined for outflow of the air and possibly of the liquid of the fluid sample, according to what has already been explained previously.

Also in embodiments of the type illustrated in FIGS. 22 and 23, then, the covering element 12 extends at least partially over the microchannels 13, but with the filter element 17 that is at least in part set between the microchannels 13 and the covering element 12. Since the element 12 is substantially impermeable to the fluid, it makes it possible in this way to confine the fluid itself inside the microchannels 13, at least between their inlet end 13a (i.e., the chamber 14) and their accumulation portion CA, at which the filter element 17 is not overlaid by the covering element 12. It should, however, be noted, with reference to embodiments of the type illustrated in FIG. 23, that the covering element 12 does not necessarily have to be overlaid at least partially on the filter element 17, it being possible for these two elements to be fixed on the substrate in adjacent positions.

Figure 24:
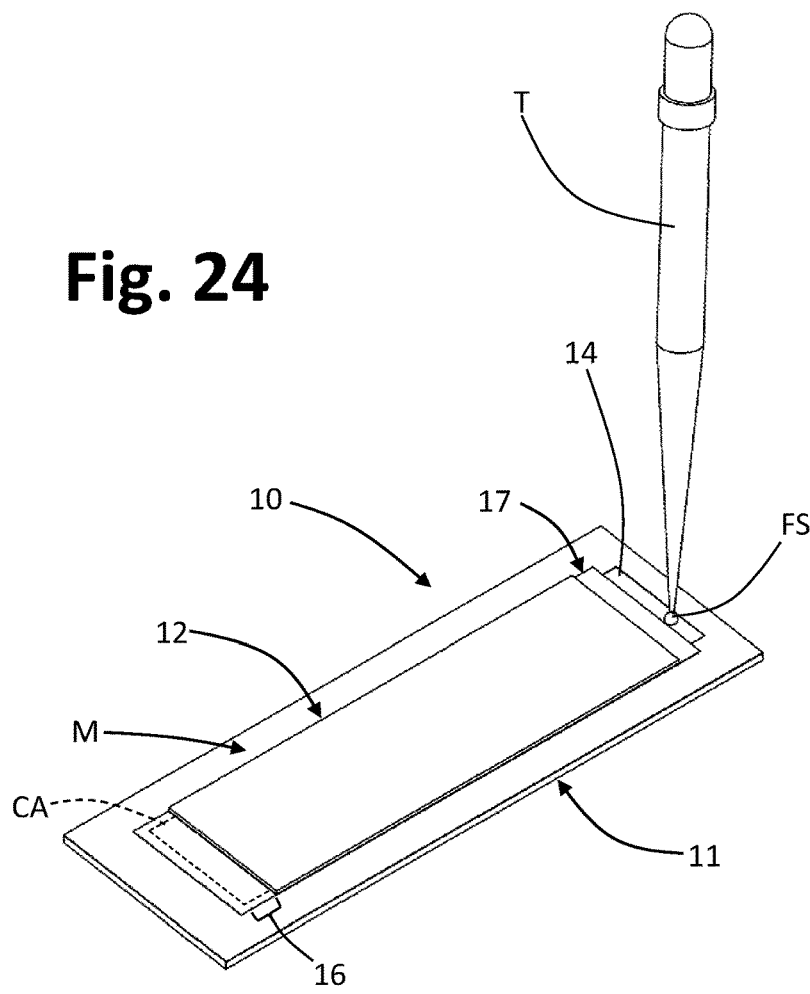
FIG. 24 is a schematic perspective view aimed at exemplifying a possible step of loading of a fluid sample into a microfluidic device of the type illustrated in FIG. 21.
Figure 25:
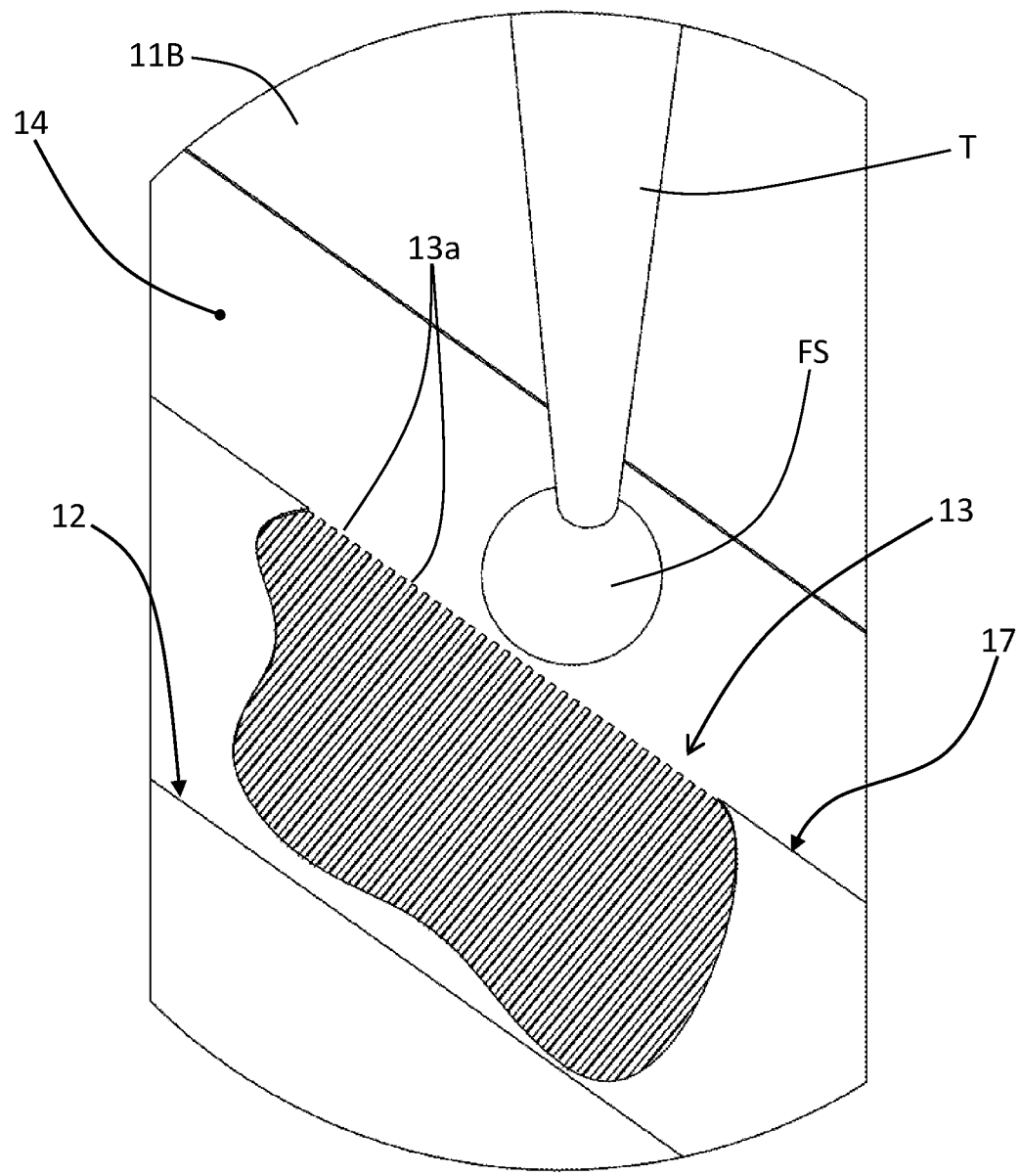
FIGS. 25 and 26 are partially sectioned schematic perspective views of a microfluidic device according to possible embodiments of the invention.

FIGS. 24-25 exemplify a possible mode of introduction of a fluid sample FS into a microfluidic device according to FIGS. 21-22, using a suitable tool T, as has already been described with reference to FIG. 8. From FIG. 24 there may in particular be appreciated the inlet ends 13a of the microchannels 13, which can be covered at the top by the filter element 17, as in the case exemplified. From the next FIG. 26 there may instead be seen the opposite end part of the microchannels 13, with their longitudinal end closed, in order to define the end region CA of accumulation of the particles following upon centrifugation.

As may be appreciated, also in this case, the concentration of the particles of interest at the end regions CA of the microchannels 13 is obtained by setting in rotation the devices 10 with respect to a centre of rotation, for example using a device 1 of the type illustrated in FIGS. 18-20.

As already mentioned, in various embodiments, microchannels 13 may extend beyond the filter element 17, in an area which is in any case closed by the covering element 12. One such case is exemplified in FIG. 26a, wherein the end regions CA of the microchannels 13 are highlighted, which extend beyond the filter element 17 but are anyway covered by the covering element 12, provided with the passageway 16. Hence, in this case, the filter element 17 and the passageway 16 are in an intermediate area of the microchannels, i.e., upstream of the corresponding closed end regions CA. The regions CA are initially full of air (or other gas or neutral liquid) which, during centrifugation, is compressed, and is able to exit partially or completely from through the filter element 17 and the way 16. At the end of the centrifugation the particles are concentrated at the bottom ends of the microchannels 13, i.e., in the regions CA not covered by the filter element 17. Hence, in embodiments of this type, the filter element may be not transparent, while at least one of the substrate 11 and the covering element 12 will be transparent, to allow for the required detections.

As mentioned, in other embodiments, a fluid sample could be forced under pressure through the microchannels of a microfluidic device according to the invention, for example using an over-pressure at inlet or a negative pressure at outlet, with respect to ambient pressure, and hence even in the absence of centrifugation. Examples of this sort are illustrated in FIGS. 27 and 28, in relation to devices 10 as that of FIG. 21.

Figure 27:
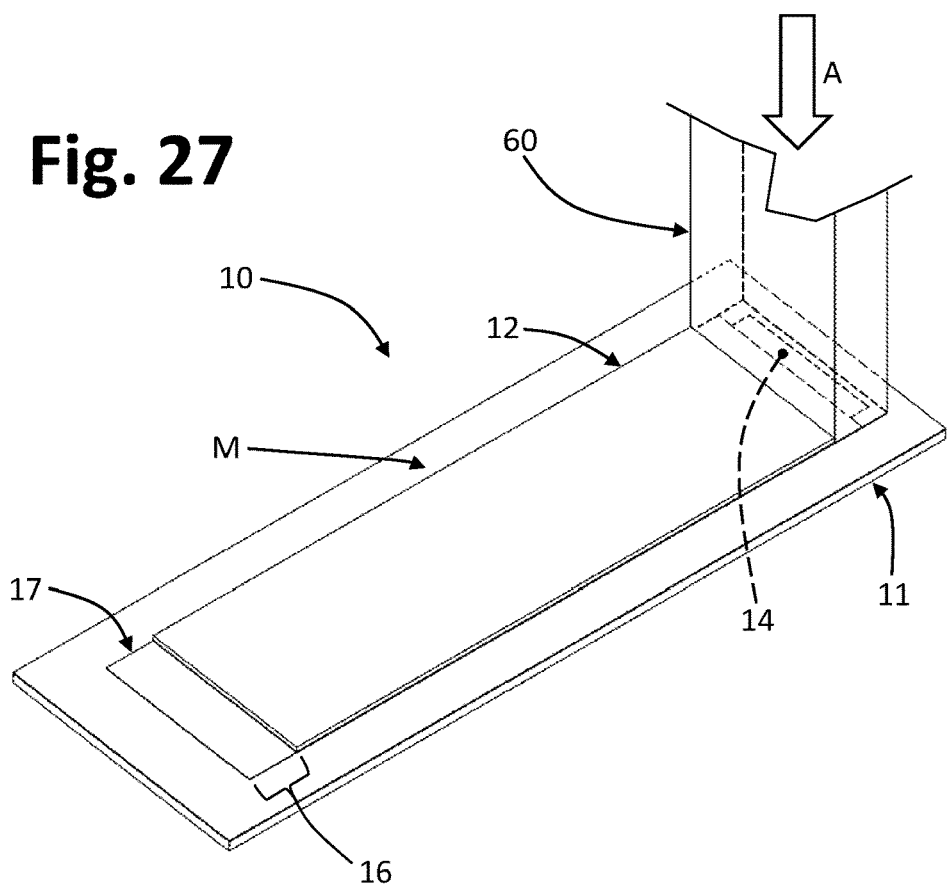
FIGS. 27 and 28 are schematic perspective views aimed at exemplifying possible modes of use of a microfluidic device according to possible embodiments of the invention.

In the case of FIG. 27 a pressure-generator system is provided for this purpose, which is only partially visible and is designated by 60 and is prearranged for generating a pressurized flow of the liquid to be treated or else a pressurized flow of air or other gas A and directing it at the chamber 14, where a sample of the fluid has previously been set. In this way, the fluid sample in the chamber 14 is forced first to penetrate into the microchannels 13 and then pass through them as far as their closed end, and then possibly exit from the passageway 16 through the corresponding portion of the filter element 17, which in this case will be permeable also to the liquid. In this way, the pressurized aeriform or fluid will bring about exit of the liquid fraction of the sample from the microchannels 13, at the end regions of which there will instead be accumulated the possible particles that are to be analysed, according to what has been described previously.

Figure 28:
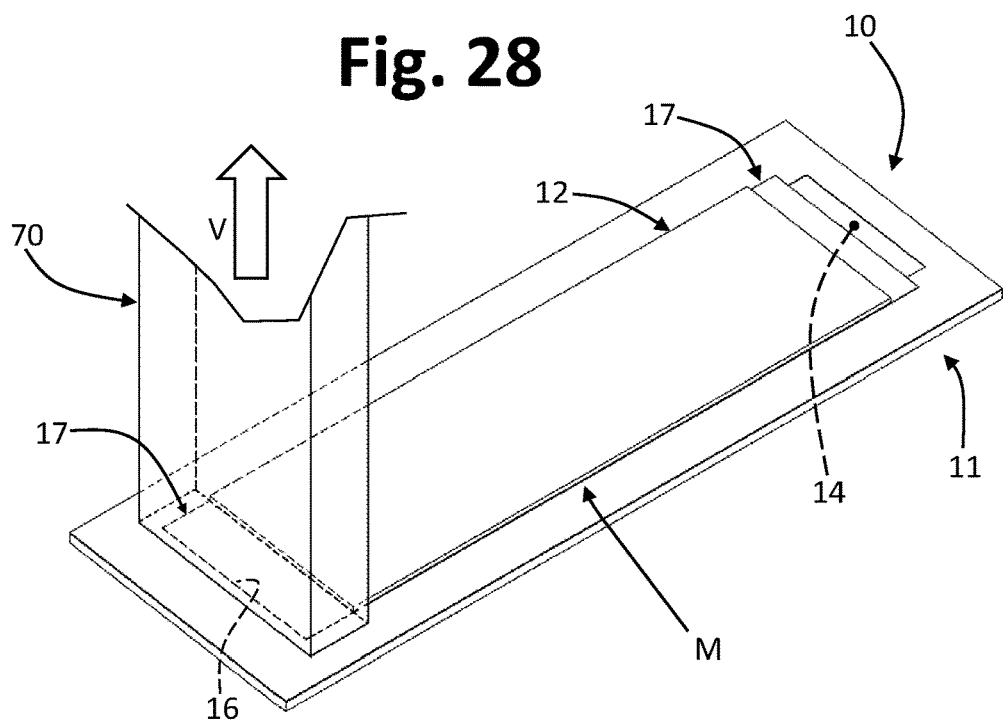

FIG. 28 exemplifies, instead, the case of a system for generating a negative pressure or vacuum, visible only partially and designated by 70, such as an aspirating syringe or a pump, which is pre-arranged for generating the vacuum or suction pressure V at the passageway 16 defined by the terminal stretch of the filter element 17, which also in this case will be permeable to the liquid.

In this way, the fluid sample previously set in the chamber 14 is drawn in thanks to the negative pressure or vacuum generated and first penetrates into the microchannels 13 and then passes through them as far as their closed end, and finally exits also in this case from the passageway 16 through the corresponding portion of the filter element 17. In this way, at the end regions of the microchannels there will instead be accumulated the possible particles that are to be analysed, whereas the liquid part will be evacuated from the device 10.

It will be appreciated that pressure-generator systems 60 and/or suction systems 70 may be used also in the case of microfluidic devices 10 of the type illustrated in FIG. 3.

In various embodiments, the microchannels of the microfluidic arrangements M are used only for detection of particles of interest contained in the fluid sample, whereas in other embodiments the microchannels can be exploited also as culture wells, in particular in the case where the particles that are to be detected are micro-organisms capable of reproduction. Alternatively, some microchannels may be "loaded" with biological materials (for example, bacteria) that the device have been induced to proliferate outside the device or have been inhibited by antibiotics.

In various embodiments, to at least one microchannel, or to each microchannel, there can be associated at least two electrodes, in particular at least at a respective end region CA. These electrodes may be electrodes for detection or else electrodes for manipulation of the particles.

For instance, in various embodiments, at least one pair of electrodes at an end region CA may be used to carry out reading of amounts of particles via detection of an electrical impedance. It is also possible to carry out differential readings by positioning further pairs of electrodes in portions of the microchannel comprised between the corresponding ends in order to make it possible to distinguish the contribution to the electrical impedance represented by the particles from the contribution represented by the fluid of the sample. In the cases where the fluid sample is a culture medium or a physiological solution, the electrical conductivity is relatively high on account of the ions dissolved in the fluid.

Pairs of electrodes positioned in such a way that an electrode of the pair is in a position corresponding to the part of the microchannel closer to the corresponding inlet end 13a and the other electrode of the pair is in the proximity of the end region, also enable verification of whether the microchannel is filled properly with the fluid containing the particles to be counted (this verification is relatively easy, considering that the fluid has in general a conductivity much higher than that of air, which is an insulator). Preferably, also the electrodes, when envisaged, are made at least in part of an electrically conductive transparent material.

Given that the device 10 according to the invention can be used for accumulating cells in a precise position (i.e., at the end accumulation regions CA), electrodes of the type referred to can be used also for carrying out manipulations on the cells themselves, for example electroporation, or else to keep them in position by means of dielectrophoresis.

As already mentioned, a microfluidic device 10 according to the invention may be used for the purposes of simple counting and/or detection of the type of the particles contained in the fluid sample, or also for more complex functions of analysis, for instance for carrying out antibiograms (in which case the microchannels could also be pre-treated, for example by introducing antibiotics therein).

The microfluidic devices and the centrifugation and/or detection devices according to the invention may advantageously be used for the purposes of evaluation of the capacity for proliferation of bacteria and microbes and, subordinately, for the purposes of determining a profile of susceptibility thereof to antibiotics (antibiogram) in short times and with small volumes of the sample fluid.

The methodologies known for this purpose are based upon evaluation of the capacity of a microbe or of a bacterium to form colonies in a medium suited to its growth, or upon evaluation of the turbidity of a culture broth following upon proliferation of the microbe. The capacity of an antibiotic to inhibit proliferation of a microbe or of a bacterium is evaluated classically by counting the corresponding colonies or on the level of turbidity of the corresponding culture broth, which are characteristics that vary as a function of the susceptibility of the microbe or bacterium to antibiotics.

This susceptibility is linked to the capacity of the antibiotic to inhibit efficient proliferation of a bacterial strain, and it is evident that the times linked to this type of analysis depend upon the speed at which the microbe or bacterium proliferates. The approach followed according to the prior art is essentially based upon the fact that a "two-dimensional" layer of bacteria or microbes (a colony) can grow until it becomes visible to the naked eye, or upon the fact that proliferation of the bacteria or microbes in a liquid can be such as to modify, in a statistically significant way, the turbidity of the liquid itself, this turbidity being measurable by means of photometry in the turbidity range (the reading is typically made at a wavelength of between 500 and 600 nm).

The techniques proposed herein, which exploit the microfluidic devices described previously, are based, instead, upon some parameters that do not consider either the two-dimensional growth of the layer of bacteria or microbes or the growth in the liquid, which is read as increase in turbidity.

More in particular, the methodologies proposed herein envisage:

i) obtaining a short-term growth of the biological material (for example, urines directly collected by the patient), with or without the addition of growth factors (for example, bacterial culture broth, such as BH);

ii) introducing the culture obtained in the previous step into the microchannels 13, which are seeded with the same concentration of biological material and/or culture medium (for this purpose, it may be particularly advantageous to provide microwells in the microchannels 13);

iii) measuring the proliferation of the bacteria in the microchannels 13;

iv) identifying one or more "negative" microchannels 13, i.e., ones in which only the culture medium will be added (for example, at 50% with PBS buffer or physiological solution);

v) identifying one or more "positive" microchannels 13, i.e., ones capable of verifying the proliferation capacity of the bacterial or microbial strain present in the system of microchannels 13;

vi) identifying a series of microchannels 13, containing the antibiotic, in such a way as to verify the resistance or susceptibility of the bacterial or microbial strain present in the seeded biological material to antibiotics.

Figure 26:
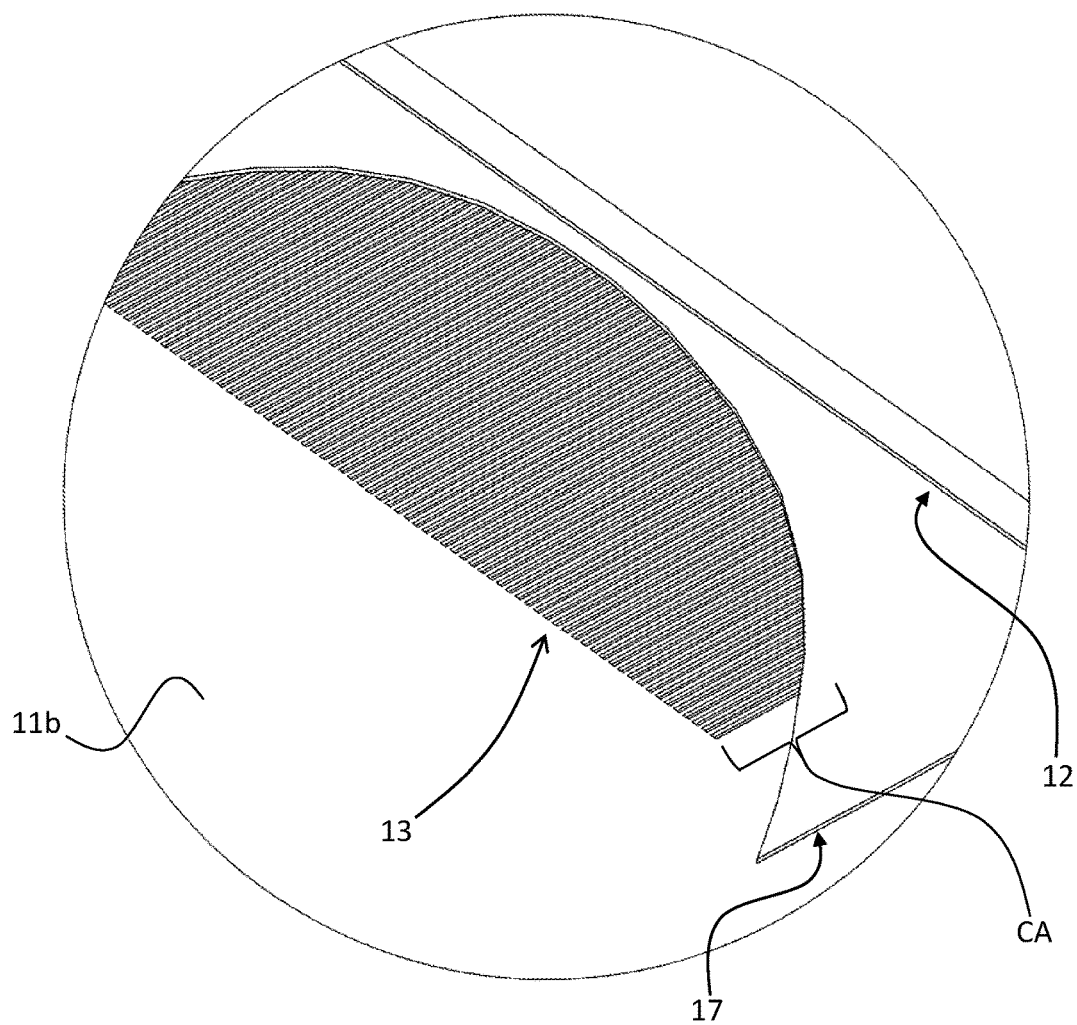
Figure 26A:
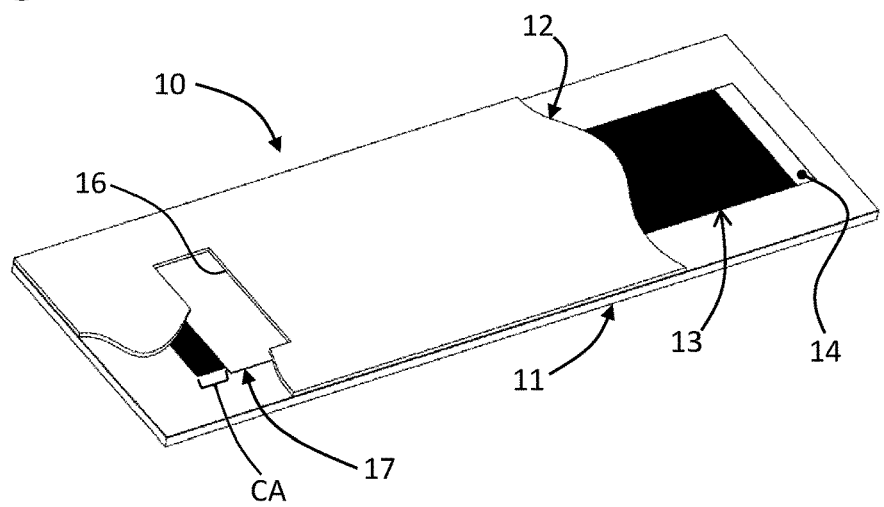
FIG. 26a is a schematic perspective view, partially sectioned, of a microfluidic device according to possible other embodiments of the invention.

The measurement of susceptibility to antibiotics may be carried out using different strategies, starting from sedimentation of the bacteria or microbes after proliferation in the accumulation regions CA of the microchannels 13, which can be obtained via centrifugation of a device 10, or else via over-pressure and/or negative pressure as explained in relation to FIGS. 26-27. This approach advantageously makes it possible to carry out the necessary comparisons between:

the amounts of bacteria or microbes present in the starting material;

the amounts of bacteria or microbes present at the end of incubation; and the amounts of bacteria or microbes present in the microchannels 13 treated with antibiotics; the use of appropriate fluorochromes may enable selective identification of live bacteria and dead bacteria.

For analyses of this sort, particularly advantageous may be supports 10 provided with a number of microfluidic arrangements, such as the support of FIG. 3. These microfluidic techniques have a higher sensitivity as compared to other techniques (for example, turbidity), given that the external stress (centrifugation, over-pressure, negative pressure) enables "concentration" of the micro-organisms in a small space, hence rendering them visible either in clear field with visible light, both in transmission and in reflection, or in fluorescence on marked cells. With the concentration technique proposed and an appropriate analysis of the image, either by means of linear arrays of sensors of by means of rectangular arrays of sensors (for example, CCD or CMOS cameras or any other technique used for image acquisition) a modification of +/−20% of the number of the cells is measured in a reliable and accurate way. Variations of this degree, which can be detected using the methodology proposed and instead cannot be detected using classic turbidity techniques, can be determined even after short growth times, for example comprised between 20 and 40 min. The quantification or estimation may be made, as has been said, via optical detections at least in the accumulation regions CA of the various microchannels 13 of interest.

In addition or as an alternative, counting of the bacterial bodies can be carried out using electrodes set in the accumulation regions CA in order to detect the modification of the impedance of an electrical field that contains a "proliferating" population of bacteria or microbes: this modification may be used as signal of the susceptibility (or resistance) of the bacterial strain under examination. Also in this case, the detection times may be extremely short.

The methodologies described above can be profitably used in situations that are extremely different from a clinical standpoint.

For instance, it is possible to measure the "absolute" number of bacteria or microbes in a sample of relatively common biological material (for example, urines for urinoculture). If, for example, a count higher than 100000 bacteria/mL is indicative of infection of the urinary ways, the mere "numerical" documentation of the bacterial charge indicates the pathological situation with great accuracy.

Also in the absence of identification of the microbe or bacterium (which can in any case be carried out with standard techniques, if necessary), the profile of susceptibility/resistance to an antibiotic panel may be easily evaluated, offering the patient the opportunity of undergoing a "non-empirical" treatment, but one based upon the study of the real antibiotic susceptibility. In this case, it is important to recall that the majority of positive urinocultures are characterised by a single isolated microbe, whereas polymicrobism is more frequent in hospitalised patients or, owing to pre-analytical causes, in patients that are complex for reasons linked to the sampling technique.

In a more complex situation (for example, in hospitalised patients), identification of the bacterium leads to an improvement in the strategies of treatment not only of the patient, but also of nosocomial infections that may be associated thereto. On the other hand, as has already been said, for less "noble" materials, like urines, identification of the pathogen can follow different pathways, whereas the profile of susceptibility to antibiotics that is not carried out in extremely short times could lead to a delay in setting up a life-saving antibiotic therapy. For this reason, the device 10 (in particular with micro-wells, as already mentioned) could be loaded with a single colony (for example, isolated from a haemoculture), which has not yet been identified but for which an immediate therapeutic approach becomes necessary. In this latter case, bacteria isolated from complex materials may be seeded, and the antibiogram could be available within some tens of minutes.

From the foregoing description, the characteristics of the present invention are clear, as likewise are its advantages.

The devices and the methodologies proposed enable operation with relatively small starting sample volumes, for example comprised between 0.05 and 1 mL. For instance, in paediatrics, in research conducted on small animals and in any case where it is useful to reduce the amount of (biological and reagent) material, also for economic reasons, it is advantageous to be able to use relatively small volumes. The measurement of a corpusculated component terminates when a number of particles are counted such as to render the problem of reproducibility virtually absent: in general, 16000 particles are counted to obtain an accurate estimate of sub-populations that are represented by 1 to 5% of the total. Hence, if it is assumed, for example, to start from a concentration of one hundred thousand particles per millilitre, according to the invention an amount of starting sample comprised between 0.2 and 0.4 mL will be sufficient, whereas, for higher concentrations, for example one million particles per millilitre, the amount of starting sample may drop, for example, to between 0.02 and 0.06 mL.

The devices according to the invention are particularly advantageous for carrying out antibiograms.

In general terms, for this purpose, a bacteria culture can be inoculated into the microchannels 13 of at least one arrangement M of a device 10. The device 10 is then subjected to centrifugation, or to over-pressure, or to negative pressure, as mentioned, and the number of bacteria that have accumulated in the regions CA of the microchannels 13 is then quantified or estimated. In applications of this sort, the microfluidic device 10 may be used exclusively for quantification of micro-organisms, for example bacteria, in so far as the proliferation in different conditions to be compared may be obtained previously, using ordinary laboratory equipment and devices.

In other applications, an antibiogram can be carried out starting from a two-dimensional culture of the bacteria on a solid support. In this case, the methodology may envisage the following steps:

i) taking a colony of bacteria from a solid-culture dish;

ii) inoculating the colony or a part thereof into a liquid medium, for example a culture broth, preferably to form a homogeneous dispersion; and iii) loading the liquid medium containing the bacteria into the microchannels 13 of at least one arrangement M of a device 10, with at least some of the aforesaid microchannels that have been previously provided with antibiotics, preferably lyophilised antibiotics of different types and/or at different concentrations, and other microchannels that have not been provided with antibiotic;

iv) incubating for a period of time ranging from 10 min to 6 h, preferably between 1 and 2 h;

v) treating the device 10 via centrifugation, or over-pressure, or negative pressure;

vi) quantifying the bacteria that have accumulated in the regions CA of the microchannels 13, in particular by carrying out a relative quantification between the microchannels 13 pre-treated with antibiotic and the ones not pre-treated, in order to obtain a profile of susceptibility of the bacteria in question to the antibiotic or antibiotics used.

Yet in other applications, the devices according to the invention can be advantageously used for carrying out an antibiogram starting from a primary sample, i.e., a sample taken directly from a subject or host organism (human or animal). In this case, the methodology may envisage the following steps:

i) obtaining a concentrate or a mass (or pellet) of bacteria from the primary sample, for example urines; for this purpose, for example, the primary sample may be subjected to centrifugation, using ordinary laboratory equipment and devices in order to separate the aforesaid bacterial mass from the surfactant; centrifugation preferably is performed in two steps: a first step at low speed to eliminate the cells; and a second step at high speed to concentrate the bacteria; alternatively, the first centrifugation step can be replaced with a filtration to eliminate the cells;

ii) inoculating the bacterial mass obtained or a part thereof into a liquid medium, for example a culture broth, preferably to form a homogeneous dispersion;

iii) loading the liquid medium containing the bacteria into the microchannels 13 of at least one arrangement M of a support 10, with at least some of the aforesaid microchannels that have been previously provided with antibiotics, preferably lyophilised antibiotics of different types and/or at different concentrations, and other microchannels that have not been provided with antibiotic;

iv) incubating for a period of time ranging from 10 min to 6 h, preferably between 1 and 2 h;

v) treating the device 10 via centrifugation, or overpressure, or negative pressure; and vi) quantifying the bacteria that have accumulated in the end regions CA of the microchannels 13, in particular by carrying out a relative quantification between the microchannels 13 pre-treated with antibiotic and the ones not pre-treated in order to obtain a profile of susceptibility of the bacteria in question to the antibiotic or antibiotics used.

It is clear that numerous variations may be made by the person skilled in the art to the supports and substrates, the devices, and the methods described herein by way of example, without thereby departing from the scope of the invention. It will likewise be evident to the person skilled in the art that individual characteristics described in relation to one embodiment may be used in other embodiments described herein, even different from the previous examples.

Application of the invention is not limited to the medical or veterinary sector, it being possible to use the supports and devices described for concentration and/or quantification of particles present in fluids of any type, for example also in the fields of industry or agriculture.

The invention claimed is:

1. A microfluidic device for concentrating particles contained in a fluid sample, comprising a monolithic substrate having a first surface at which at least one microfluidic arrangement is defined, which comprises:

a loading chamber, for loading the fluid sample into the at least one microfluidic arrangement;

a plurality of microchannels, which have respective inlet ends which extend from the loading chamber, the microchannels of the plurality of microchannels being fluidically connected in parallel to said chamber;

a covering element, which is substantially impermeable to the fluid sample and extends at the first surface at least partially over the plurality of microchannels, wherein the loading chamber and the plurality of microchannels extend substantially according to a plane identified by the monolithic substrate, wherein the loading chamber and the plurality of microchannels are surface indentations at the first surface of the monolithic substrate, the surface indentations each defining in the monolithic substrate a bottom and longitudinal side walls of a respective microchannel of the plurality of microchannels, wherein each microchannel of the plurality of microchannels is delimited, at the longitudinal end thereof opposite to the inlet end, by a respective closing wall defined by the monolithic substrate, wherein each microchannel of the plurality of microchannels has an accumulation region generally opposite to the respective inlet end, wherein a filter element, which is permeable at least to air, is set on top of the first surface of the monolithic substrate, to extend above at least a portion of all microchannels of the plurality of microchannels, to thereby define at least a corresponding portion of a top surface of each microchannel of the plurality of microchannels that extends between the longitudinal side walls of each microchannel, wherein the covering element is partially covering the filter element, to provide an uncovered portion of the filter element through which air is vented from all microchannels of the plurality of microchannels, wherein the filter element is configured for withholding within each microchannel of the plurality of microchannels the particles that may be present in the fluid sample, in such a way that the particles contained in a volume of fluid of the fluid sample that penetrates into each microchannel of the plurality of microchannels tend to concentrate in the respective accumulation region as a result of a force applied to at least one of the microfluidic device or the fluid sample loaded into the loading chamber, said force being selected from among a centrifugal force caused by a rotation of the microfluidic device about a centre of rotation, or a positive pressure applied on the fluid sample at the loading chamber, or a negative pressure applied on the fluid sample at the accumulation region of each microchannel of the plurality of microchannels.

2. The microfluidic device according to claim 1, wherein the fluid sample includes a liquid, and the covering element is sized or shaped to define at least one of the following:

a passage for introduction of the fluid sample into the loading chamber;

a passageway for exit of the liquid from the plurality of microchannels.

3. The microfluidic device according to claim 1, wherein:

at least one of the monolithic substrate and the covering element is configured for keeping the filter element in a corresponding operative position between the first surface of the monolithic substrate and the covering element.

4. The microfluidic device according to claim 1, wherein the filter element is set above only a terminal stretch of all microchannels of the plurality of microchannels, to define said top surface of each microchannel of the plurality of microchannels.

5. The microfluidic device according to claim 1, wherein each microchannel of the plurality of microchannels:
has a width of between 5 and 200 μm; and/or
has a depth or height of between 2 and 100 μm, and/or
has a length of between 5 and 50 mm.

6. The microfluidic device according to claim 1, wherein:
each microchannel of the plurality of microchannels has at least one surface portion defined by at least one of a hydrophilic material or a hydrophobic material, the hydrophilic material or the hydrophobic material belonging to at least one from among the monolithic substrate, the covering element, or the filter element; and/or
the device is made at least in part of transparent material, the transparent material belonging to at least one from among the monolithic substrate, the covering element, or the filter element.

7. The microfluidic device according to claim 1, wherein the monolithic substrate:
is configured for being mounted on a rotating member of a centrifugation and/or detection device; and/or
is substantially disk-shaped.

8. The microfluidic device according to claim 1, wherein in said first surface of the monolithic substrate a plurality of said microfluidic arrangements are defined.

9. The microfluidic device according to claim 8, wherein said plurality of microfluidic arrangements are arranged in a direction that is at least approximately radial with respect to a centre of rotation of the monolithic substrate.

10. The microfluidic device according to claim 1, wherein the microchannels of the plurality of microchannels are set side by side at a distance of between 5 and 200 μm from one another.

11. The microfluidic device according to claim 1, wherein the filter element is permeable to liquids.

12. The microfluidic device according to claim 1, wherein the monolithic substrate defines separating portions that separate each microchannel of the plurality of microchannels from one another, the separating portions having a width of between 5 and 200 μm.

13. A system for concentrating particles contained in a fluid sample, comprising a microfluidic device according to claim 1 and a centrifugation device, the centrifugation device having a rotating member configured for setting in rotation said microfluidic device.

14. A system for detecting particles contained in a fluid sample, comprising a microfluidic device according to claim 1 and a detection device, the detection device having a rotating member configured for subjecting to an angular movement said microfluidic device, and optical sensor means configured for carrying out optical detections on the microfluidic device or detecting particles that have accumulated in one or more accumulation regions of the microfluidic device,
wherein the optical sensor means are configured for acquiring an optical signal or an image of said one or more accumulation regions of the microfluidic device, and
wherein the detection device is pre-arranged for processing, on the basis of said optical signal or image, information representing an amount of particles that have accumulated in said one or more accumulation regions.

15. A method for detection of particles that may be present in a fluid sample, comprising the steps of:
a) providing a microfluidic device according to claim 1;
b) introducing a volume of the fluid sample into the loading chamber of at least one microfluidic arrangement of the microfluidic device;
c) subjecting the microfluidic device to a centrifugation, or subjecting the corresponding fluid sample to a positive pressure or a negative pressure, respectively at the loading chamber or at accumulation regions of first microchannels of the plurality of microchannels; and
d) detecting particles possibly accumulated in the accumulation region of each first microchannel, in an optical and/or electrical way.

16. The method according to claim 15, wherein:
step b) comprises providing a liquid medium containing micro-organisms, or microbes, or bacteria of at least one bacterial strain; and
step d) comprises quantifying the number of micro-organisms, or microbes, or bacteria that have accumulated in the accumulation region of each first microchannel.

17. The method according to claim 16, comprising the operations of:
i) pre-treating said first microchannels with at least one first antibiotic;
ii) obtaining a mass of micro-organisms, or microbes, or bacteria;
iii) inoculating at least one part of said mass into the liquid medium;
iv) introducing a volume of the liquid medium into said first microchannels;
iv) waiting for a period of time comprised between 10 min and 6 h;
v) subjecting the microfluidic device to a centrifugation, or subjecting the corresponding fluid sample to a positive pressure or a negative pressure, respectively at the loading chamber or at the accumulation regions of the microchannels;
vi) quantifying the number of micro-organisms, or microbes, or bacteria that have accumulated in the accumulation regions of said first microchannels, by carrying out a relative quantification between said first microchannels and second microchannels of the microfluidic device that have not been pre-treated with the at least one first antibiotic, in order to obtain a susceptibility profile of said micro-organisms, or microbes, or bacteria to the at least one first antibiotic.

18. A microfluidic device for concentrating particles contained in a fluid sample, comprising a monolithic substrate having a first surface at which at least one microfluidic arrangement is defined, which comprises:
a loading chamber, for loading the fluid sample into the at least one microfluidic arrangement;
a plurality of microchannels, which have respective inlet ends which extend from the loading chamber, the microchannels of the plurality of microchannels being fluidically connected in parallel to said chamber;
a covering element, which is substantially impermeable to the fluid sample and extends at the first surface at least partially over the plurality of microchannels, the covering element having a peripheral profile,
wherein the loading chamber and the plurality of microchannels extend substantially according to a plane identified by the monolithic substrate,
wherein the loading chamber and the plurality of microchannels are surface indentations at the first surface of the monolithic substrate, the surface indentations each defining a bottom and longitudinal side walls of a respective microchannel of the plurality of microchannels, wherein each microchannel of the plurality of microchannels is delimited, at the longitudinal end thereof opposite to the inlet end, by a respective closing wall defined by the monolithic substrate, wherein each microchannel of the plurality of microchannels has an accumulation region generally opposite to the respective inlet end, wherein a filter element which is permeable at least to air is set on top of the first surface of the substrate, to extend above at least a portion of all microchannels of the plurality of microchannels, and thereby define at least a corresponding portion of a top surface of each microchannel of the plurality of microchannels that bridges the longitudinal side walls of each microchannel, wherein the filter element has a covered portion and an uncovered portion, the covered portion being set between the first surface of the monolithic substrate and the covering element, wherein each microchannel of the plurality of microchannels has a terminal portion which includes the longitudinal end thereof, wherein the terminal portion of each microchannel of the plurality of microchannels and the uncovered portion of the filter element both extend beyond the peripheral profile of the covering element, such that air is vented from all microchannels of the plurality of microchannels through the uncovered portion of the filter element, wherein the filter element is configured for withholding within each microchannel of the plurality of microchannels the particles that may be present in the fluid sample, in such a way that the particles contained in a volume of fluid of the fluid sample that penetrates into each microchannel of the plurality of microchannels tend to concentrate in the respective accumulation region as a result of a force applied to at least one of the microfluidic device or the fluid sample loaded into the loading chamber, said force being selected from among a centrifugal force caused by a rotation of the microfluidic device about a centre of rotation, or a positive pressure applied on the fluid sample at the loading chamber, or a negative pressure applied on the fluid sample at the accumulation region of each microchannel of the plurality of microchannels, wherein the monolithic substrate defines separating portions that separate each microchannel of the plurality of microchannels from one another, the uncovered portion of the filter element extending above a corresponding part of all said separating portions.

19. The microfluidic device according to claim 18, being configured for concentrating particles selected from whole blood cells, or bacteria, or yeasts, and wherein:

the particles to be concentrated are whole blood cells, and each microchannel of the plurality of microchannels has a depth or height of 10 and 20 μm, or the particles to be concentrated are bacteria, and each microchannel of the plurality of microchannels has a depth or height of between 3 and 10 μm, or the particles to be concentrated are yeasts, and each microchannel of the plurality of microchannels has a depth or height of between 5 and 20 μm.

* * * * *